(12) United States Patent
Gray et al.

(10) Patent No.: US 12,359,219 B2
(45) Date of Patent: *Jul. 15, 2025

(54) TRANSGENE CASSETTES DESIGNED TO EXPRESS A HUMAN MECP2 GENE

(71) Applicant: THE BOARD OF REGENTS OF THE UNIVERSITY OF TEXAS SYSTEM, Austin, TX (US)

(72) Inventors: Steven J. Gray, Southlake, TX (US); Sarah Sinnett, Farmers Branch, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/411,647

(22) Filed: Jan. 12, 2024

(65) Prior Publication Data
US 2024/0191254 A1 Jun. 13, 2024

Related U.S. Application Data

(63) Continuation of application No. 17/112,299, filed on Dec. 4, 2020, now Pat. No. 11,891,616.

(60) Provisional application No. 62/944,209, filed on Dec. 5, 2019, provisional application No. 62/946,696, filed on Dec. 11, 2019, provisional application No. 63/008,159, filed on Apr. 10, 2020, provisional application No. 63/047,596, filed on Jul. 2, 2020.

(51) Int. Cl.
*C12N 15/86* (2006.01)
*C12N 15/113* (2010.01)

(52) U.S. Cl.
CPC ............ *C12N 15/86* (2013.01); *C12N 15/113* (2013.01); *C12N 2310/141* (2013.01); *C12N 2310/315* (2013.01); *C12N 2310/321* (2013.01)

(58) Field of Classification Search
CPC ........................... C12N 15/86; C12N 15/8645
See application file for complete search history.

(56) References Cited

U.S. PATENT DOCUMENTS

| | | |
|---|---|---|
| 2013/0225666 A1 | 8/2013 | Kaspar et al. |
| 2016/0175462 A1 | 6/2016 | Zhang et al. |
| 2021/0170051 A1† | 6/2021 | Gray |

FOREIGN PATENT DOCUMENTS

| | | | |
|---|---|---|---|
| WO | 2009126563 A1 | 10/2009 | |
| WO | 2018172794 A1 | 9/2018 | |
| WO | 2018172795 A1 | 9/2018 | |
| WO | 20182265785 A1 | 12/2018 | |
| WO | WO-2019222444 A2 * | 11/2019 | ........... C07K 14/005 |
| WO | 2020047234 † | 3/2020 | |
| WO | 2020047234 A1 | 3/2020 | |
| WO | 2020219990 A1 | 10/2020 | |

OTHER PUBLICATIONS

Gadalla et al, "Improved survival and reduced phenotypic severity following AAV9/MECP2 gene transfer to neonatal and juvenile Mecp2 knockout mice", Molecular Therapy, vol. 21, No. 1, pp. 18-30, Jan. 2013.
Gadalla et al, "Development of a Novel AAV Gene Therapy Cassette with Improved Safety Features and Efficacy in a Mouse Model of Rett Syndrome", Molecular Therapy Methods & Clinical Development, vol. 5, pp. 180-190, Jun. 2017.
McGowan et al, "Regulatory functions and pathological relevance of the MECP2 3' UTR in the central nervous system", Cell Regeneration, vol. 4, No. 1, pp. 1-10, (2015).
PCT International Application No. PCT/US2020/063300, International Search Report of the International Searching Authority, dated Apr. 6, 2021, 5 pages.
PCT International Application No. PCT/US2020/063300, Written Opinion of the International Searching Authority, dated Apr. 6, 2021, 5 pages.
Sinnett et al., "Improved MECP2 gene therapy extends the survival of MeCP2-null mice without apparent toxicity after intracisternal delivery", Molecular Therapy: Methods & Clinical Developemtn, vol. 5, pp. 106-115, Jun. 2017.
Tillotson et al, "Radically truncated MeCP2 rescues Rett syndrome-like neurological defects", Nature, vol. 550, No. 7676, pp. 398-401, Oct. 19, 2017.
Zhang, F. & Wang, D., (2017) The pattern of microRNA binding site distribution. Genes, 8(11), 296. (Year:2017).
International Preliminary Report on Patentability issued in International Application No. PCT/US2020/063300, date Jun. 16, 2022, 8 pages.

\* cited by examiner
† cited by third party

*Primary Examiner* — Christopher M Babic
*Assistant Examiner* — Jennifer S Spence
(74) *Attorney, Agent, or Firm* — DLA Piper LLP US

(57) ABSTRACT

The present disclosure provides methods and compositions for the treatment of diseases and genetic disorders linked to MeCP2 loss and/or misfunction, including RETT syndrome. The methods and compositions of the present disclosure comprise rAAV vectors and rAAV viral vectors comprising transgene nucleic acid molecules comprising nucleic acid sequences encoding for a MeCP2 polypeptide.

20 Claims, 26 Drawing Sheets
Specification includes a Sequence Listing.

| ICM treatment | Clasping Score at 4-8 weeks of age | | |
|---|---|---|---|
| | 4 weeks (pre-ICM) | 6 weeks | 8 weeks |
| 0 vg, n=6 | 0.0 ± 0.0 | 0.0 ± 0.0 | 0.0 ± 0.0 |
| 1E12 vg AAV9/miniMECP2, n=5 | 0.0 ± 0.0 | 0.6 ± 0.2*,# | 0.8 ± 0.4*,# |
| 1E12 vg PHP.B/miniMECP2, n=5 | 0.0 ± 0.0 | 1.6 ± 0.2*,# | 2.0 ± 0.0*,# |

Number of miRNA targets shared between pairs of 3' UTRs from 10 randomly selected human genes

| | ACTB | ATF1 | HSPA4 | MRPL9 | POLR1C | PRKAG1 | RPL5 | DAD1 | GAPDH | DARS | |
|---|---|---|---|---|---|---|---|---|---|---|---|
| | | 71 | 151 | 259 | 43 | 130 | 53 | 137 | 45 | 22 | *ACTB* |
| | | | 36 | 67 | 9 | 46 | 24 | 31 | 6 | 16 | *ATF1* |
| | | | | 99 | 16 | 58 | 29 | 87 | 14 | 4 | *HSPA4* |
| | | | | | 22 | 107 | 62 | 94 | 34 | 19 | *MRPL9* |
| | | | | | | 24 | 11 | 26 | 14 | 3 | *POLR1C* |
| | | | | | | | 34 | 41 | 27 | 15 | *PRKAG1* |
| | | | | | | | | 28 | 8 | 12 | *RPL5* |
| | | | | | | | | | 25 | 10 | *DAD1* |
| | | | | | | | | | | 1 | *DAD1* |

Number of targets shared between pairs of 3' UTRs for human genes mediating intellectual ability

| MEF2C | NSD1 | RPS6KA3 | ZEB2 | MBD5 | DYRK1A | TCF4 | ATRX | UBE3A | SLC6A1 | |
|---|---|---|---|---|---|---|---|---|---|---|
| 1009 | 971 | 936 | 760 | 886 | 860 | 819 | 605 | 434 | 505 | MECP2 |
| | 707 | 814 | 722 | 794 | 722 | 761 | 563 | 377 | 422 | MEF2C |
| | | 666 | 531 | 649 | 602 | 592 | 465 | 283 | 361 | NSD1 |
| | | | 609 | 741 | 663 | 669 | 497 | 347 | 377 | RPS6KA3 |
| | | | | 602 | 578 | 610 | 474 | 320 | 319 | ZEB2 |
| | | | | | 625 | 681 | 511 | 353 | 371 | MBD5 |
| | | | | | | 630 | 451 | 344 | 367 | DYRK1A |
| | | | | | | | 482 | 341 | 354 | TCF4 |
| | | | | | | | | 262 | 235 | ATRX |
| | | | | | | | | | 168 | UBE3A |

FIG. 6B

| Number of shared miRNA targets, normalized against UTR length | DARS | ACTB | ATF1 | HSPA4 | MRPL9 | POLR1C | PRKAG1 | RPL5 | DAD1 | GAPDH | |
|---|---|---|---|---|---|---|---|---|---|---|---|
| DARS |  | 12 | 11 | 13 | 11 | 11 | 8 | 13 | 16 | 10 | DARS |
| ACTB | 3 |  | 3 | 3 | 2 | 4 | 4 | 3 | 2 | 7 | ACTB |
| ATF1 | 6 | 6 |  | 5 | 4 | 5 | 5 | 8 | 5 | 2 | ATF1 |
| HSPA4 | 11 | 11 | 7 |  | 5 | 9 | 10 | 9 | 12 | 8 | HSPA4 |
| MRPL9 | 2 | 1 | 1 | 1 |  | 2 | 2 | 2 | 5 | 1 | MRPL9 |
| POLR1C | 5 | 8 | 4 | 5 | 5 |  | 5 | 4 | 10 | 7 | POLR1C |
| PRKAG1 | 2 | 4 | 2 | 3 | 3 | 6 |  | 3 | 3 | 5 | PRKAG1 |
| RPL5 | 6 | 5 | 6 | 5 | 6 | 6 | 4 |  | 9 | 4 | RPL5 |
| DAD1 | 2 | 1 | 1 | 2 | 3 | 3 | 1 | 2 |  | 0 | DAD1 |
| GAPDH | 1 | 3 | 0 | 1 | 1 | 1 | 2 | 1 | 0 |  | GAPDH |

TRANSGENE CASSETTES DESIGNED TO EXPRESS A HUMAN MECP2 GENE

CROSS REFERENCE TO RELATED APPLICATIONS

This application is a continuation of U.S. patent application Ser. No. 17/112,299, filed Dec. 4, 2020, which claims priority to U.S. Provisional Application No. 62/944,209, filed Dec. 5, 2019, U.S. Provisional Application No. 62/946,696, filed Dec. 11, 2019, U.S. Provisional Application No. 63/008,159, filed Apr. 10, 2020 and U.S. Provisional Application No. 63/047,596, filed Jul. 2, 2020. The contents of each of the aforementioned patent applications are incorporated by reference herein in their entireties for all purposes.

INCORPORATION BY REFERENCE OF SEQUENCE LISTING

The instant application contains a Sequence Listing which has been submitted in XML format via EFS-Web and is hereby incorporated by reference in its entirety. Said XML copy, created on Jan. 11, 2024 is named "426871-000371_Seq_List.xml" and is about 39.8 KB in size.

BACKGROUND

Rett Syndrome is caused by mutations in the X-linked MECP2, a gene encoding a protein (MeCP2) that regulates expression of many genes involved in normal brain function, particularly the maintenance of synapses. Prevalence of Rett Syndrome is 1/9,000 in girls under the age of 12, whereas prevalence in the general population is an estimated at 1/30,000. The age of onset is about 6-18 months. Normal development occurs for a brief period, followed by loss of speech and purposeful hand use, stereotypic hand movements, and gait abnormalities. Additional features include deceleration of head growth, seizures, autistic features, and breathing abnormalities. MECP2 gene transfer has been shown to extend the survival of Mecp2$^{-/y}$ knockout (KO) mice modeling Rett syndrome (RTT), an X-linked neurodevelopmental disorder. However, controlling deleterious overexpression of MeCP2 remains the critical unmet obstacle towards a safe and effective gene therapy approach for RTT. Compositions and methods are needed in the art for the gene therapy treatment of Rett Syndrome.

SUMMARY

The present disclosure provides an rAAV vector, comprising, in the 5' to 3' direction: a) a first AAV ITR sequence; b) a promoter sequence; c) a transgene nucleic acid molecule; d) a regulatory sequence; and e) a second AAV ITR sequence.

A transgene nucleic acid molecule can comprise a nucleic acid sequence encoding for an MeCP2-derived polypeptide, wherein the MeCP2-derived polypeptide is a miniMeCP2 polypeptide. A miniMeCP2 polypeptide can comprise the amino acid sequence set forth in SEQ ID NO: 1. A nucleic acid sequence encoding for an MeCP2 polypeptide and/or MeCP2-derived polypeptide can comprise the nucleic acid sequence set forth in SEQ ID NO: 3. A nucleic acid sequence encoding for an MeCP2 polypeptide and/or MeCP2-derived polypeptide can comprise the nucleic acid sequence set forth in SEQ ID NO: 28.

A first AAV ITR sequence can comprise the nucleic acid sequence set forth in SEQ ID NO: 18. A second AAV ITR sequence can comprise the nucleic acid sequence set forth in SEQ ID NO: 20.

A promoter sequence can comprise an MeP426 promoter sequence. An MeP426 promoter sequence can comprise the nucleic acid sequence set forth in SEQ ID NO: 22.

A regulatory sequence can comprise one or more miRNA binding sites. An miRNA binding site can comprise an miR-9-5p miRNA binding site, a miR-26b-5p miRNA binding site, a miR-23a-3p miRNA binding site, a miR-218-5p miRNA binding site, a miR-27a-3p miRNA binding site, a let-7e-5p miRNA binding site, a miR-98-5p miRNA binding site, a let-7d-5p miRNA binding site, a let-7g-5p miRNA binding site, a miR-218-5p miRNA binding site or any combination thereof.

A regulatory sequence can comprise one or more of the nucleic acid sequences set forth in SEQ ID NOs: 7, 8, 9, 10, 11, and 12. A regulatory sequence can comprise each of the nucleic acid sequences set forth in SEQ ID NOs: 7, 8, 9, 10, 11, and 12. A regulatory sequence can comprise the nucleic acid sequence set forth in SEQ ID NO: 13. A regulatory sequence can comprise the nucleic acid sequence set forth in SEQ ID NO: 14. A regulatory sequence can comprise the nucleic acid sequence set forth in SEQ ID NO: 15. A regulatory sequence can comprise the nucleic acid sequence set forth in SEQ ID NO: 16. A regulatory sequence can comprise, in the 5' to 3' direction: i) the nucleic acid sequence set forth in SEQ ID NO: 15; ii) the nucleic acid sequence set forth in SEQ ID NO: 13; and iii) the nucleic acid sequence set forth in SEQ ID NO: 16. A regulatory sequence can comprise the nucleic acid sequence set forth in SEQ ID NO: 17.

The present disclosure provides an rAAV vector, comprising, in the 5' to 3' direction: a) a first AAV ITR sequence comprising the nucleic acid sequence set forth in SEQ ID NO: 18; b) a promoter sequence comprising an MeP426 promoter sequence, wherein the MeP426 comprises the nucleic acid sequence set forth in SEQ ID NO: 22; c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1; d) a regulatory sequence comprising the nucleic acid sequence set forth in SEQ ID NO: 13; and e) a second AAV ITR sequence comprising the nucleic acid sequence set forth in SEQ ID NO: 20.

The present disclosure provides an rAAV vector, comprising, in the 5' to 3' direction: a) a first AAV ITR sequence comprising the nucleic acid sequence set forth in SEQ ID NO: 18; b) a promoter sequence comprising an MeP426 promoter sequence, wherein the MeP426 comprises the nucleic acid sequence set forth in SEQ ID NO: 22; c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1; d) a regulatory sequence comprising the nucleic acid sequence set forth in SEQ ID NO: 17; and e) a second AAV ITR sequence comprising the nucleic acid sequence set forth in SEQ ID NO: 20.

The present disclosure provides an rAAV viral vector comprising: a) any one of the rAAV vectors described herein; and b) an AAV capsid protein. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein. An AAV capsid protein can be an AAV9 capsid protein. An AAV capsid protein can be an AAVPHP.B capsid protein.

The present disclosure provides a pharmaceutical composition comprising: any rAAV viral vector described herein and at least one pharmaceutically acceptable excipient and/or additive.

The present disclosure provides methods for treating a subject having a disease and/or disorder involving a MECP2 gene, the method comprising administering to the subject at least one therapeutically effective amount of any rAAV viral vector described herein or any pharmaceutical composition described herein. An rAAV viral vector or pharmaceutical composition can be administered to a subject at a dose ranging from about 105 to about 1020 viral vector particles. An rAAV viral vector or pharmaceutical composition can be administered to a subject at a dose ranging from about 105 to about $10^{15}$ viral vector particles. An rAAV viral vector or pharmaceutical composition can be administered to a subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. An rAAV viral vector or pharmaceutical composition can be administered intrathecally. An rAAV viral vector or pharmaceutical composition can be administered intracranially.

The present disclosure provides any rAAV viral vector described herein or any pharmaceutical composition described herein for use in treating a disease and/or disorder involving a MECP2 gene in a subject in need thereof. An rAAV viral vector or a pharmaceutical composition can be for administration to the subject at a dose ranging from about $10^{11}$ to about $10^{18}$ viral vector particles. An rAAV viral vector or a pharmaceutical composition can be for administration to the subject at a dose ranging from about 105 to about 1020 viral vector particles. An rAAV viral vector or pharmaceutical composition can be for administration to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. An rAAV viral vector or pharmaceutical composition can be for administration intrathecally. An rAAV viral vector or pharmaceutical composition can be for administration intracranially.

A disease and/or disorder involving the MECP2 gene can be Rett Syndrome.

Any of the above aspects, or any other aspect described herein, can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 1A-C shows miniMECP2 vectors cause side effects in wildtype (WT) mice. FIG. 1A is a table depicting increased mean clasping score in mice following AAV9/miniMECP2 treatment in an acute toxicity study. Overexpression of miniMeCP2 caused significant increases in abnormal clasping scores. n=5-6 mice per group. Saline versus virus treatments; and pre-versus post-injection: #p<0.05. FIG. 1B is a photograph depicting severe hindlimb clasping observed 3 days after treatment with PHP.B/miniMECP2 ($1\times10^{12}$ vg/mouse, ICM). In healthy mice, hindlimbs extend outward. FIG. 1C is graph depicting changes in aggregate phenotype severity score in mice following treatment with AAV9/and PHP.B/miniMECP2. Both AAV9/and PHP.B/miniMECP2 significantly increase aggregate phenotype severity scores within 2 weeks post-injections (p<0.05). FIGS. 1A-1C show data for mice housed and treated at UNC-Chapel Hill. All other mice in this application were tested at UTSW. FIG. 1A and FIG. 1C are means±SEMs.

FIG. 2A is a graph depicting the incidence of 451 miRNA targets; many miRNA targets appear frequently across the curated list of 3' UTRs. FIG. 2B is a plot depicting that among 2491 human targets and 1831 mouse targets, 451 targets had identical annotation across both mouse and human 3' UTR data sets. The scatter plot shows the same data as that shown in FIG. 2A. Targets that are annotated in over half of the examined 3' UTR sequences for both species were prioritized for target panel design (shaded area). Within the shaded area, black data points indicate targets corresponding to miRNAs expressed at moderate to high levels in dissected CC, cerebellar, and/or medullary tissue (signal intensity >500). Square data points indicate targets for putative MeCP2- responsive miRNAs (let-7e-5p*, miR-98-5p, miR-26b-5p, let-7d-5p, let-7g-5p, miR-23a-3p) as well as 2 additional miRNAs (miR-9-5p and miR-27a-3p; indicated by #) which were increased in cervical cord when data for MeCP2(−) and MeCP2(+) treatment groups were aggregated together (data not shown). MeCP2(−) groups, for example, would include both saline-treated and AAV9/EGFP-treated KO mice. For clarity, we have limited notation (black and square data points) to the shaded area only. A target for miR-218-5p was included in the new panel design ("miRARE"; elsewhere noted as "Reg2") for the purpose of making miRARE more broadly applicable for multiple gene therapy applications. Expression of miR-218-5p did not appear to be MeCP2-responsive in our HTS data. FIG. 2C is a schematic of the miniMECP2-miRARE viral genome cassette. Dotted black and solid white lines indicate miRNA targets that are part of RDH1pA. Solid gray lines indicate miRARE targets that were inserted into RDH1pA. ITR, inverted terminal repeat; sc, mutated self-complementary ITR sequence.

FIG. 3A is a graph depicting that AAV9/miniMECP2-treated WT mice ($1 \times 10^{12}$ vg/mouse) had significantly lower weight than that of saline-treated WT mice beginning at 15 weeks of age (p<0.05). No significant difference was observed between saline- and AAV9/miniMECP2-miRARE-treated WT mice ($1 \times 10^{12}$ vg/mouse). The same legend also applies to FIG. 3B. FIG. 3B is a graph depicting that AAV9/MECP2- and AAV9/miniMECP2-treated WT mice had a significantly higher mean aggregate behavioral severity score versus that observed for saline-treated mice (p<0.05; at 6-30 and 7-27 weeks of age, respectively). AAV9/miniMECP2-miRARE-treated WT mice had a significantly lower mean aggregate severity score versus those of AAV9/MECP2- and AAV9/miniMECP2-treated mice at most timepoints from 11-19 and 9-20 weeks of age, respectively. No significant difference was observed between saline- and AAV9/miniMECP2-miRARE-treated WT mice ($1 \times 10^{12}$ vg/mouse). FIG. 3C is a graph depicting that most WT mice treated with AAV9/miniMECP2-miRARE did not develop severe clasping abnormalities (n=2/9 mice). FIG. 3D is a graph depicting that WT mice treated with AAV9/miniMECP2-miRARE did not develop severe gait abnormalities (n=0/9 mice). In FIG. 3C and FIG. 3D, severe abnormal gait and severe clasping are each scored as a 2 on a scale of 0-2. All vectors were administered at $1 \times 10^{12}$ vg/mouse. Mice that were euthanized early prior to developing severe gait or clasping scores were excluded from FIG. 3C and FIG. 3D. * p<0.05 using Gehan-Breslow-Wilcoxon test, which can be used to evaluate significance for Kaplan-Meier plots. A one-way ANOVA of mean age-of-onset for FIG. 3D is not encouraged, as there are no timepoints at which AAV9/miniMECP2-miRARE-treated WT mice develop severe gait abnormalities. FIG. 3E depicts that no early deaths have been observed for AAV9/miniMECP2-miRARE-treated WT mice. MiRARE groups are offset for clarity. Diamonds indicate veterinarian-requested euthanasias for bullying-related injuries (saline-treated) and for prolapses (AAV9/miniMECP2-treated). Prolapses were observed in 8-17% of AAV9/miniMECP2-treated WT mice ($1 \times 10^{11}$-$1 \times 10^{12}$ vg, respectively). Four AAV9/MECP2-treated mice were dissected at 8 weeks of age and were therefore excluded from the survival plot. Data in FIG. 3A and FIG. 3B are means±SEMs. For simplicity only statistical differences between saline- and high dose-treated WT mice were analyzed. *p<0.05.

FIG. 4A is a graph survival in mice treated with MECP2 compositions of the disclosure. Diamonds indicate veterinarian-requested euthanasias, which were primarily for severe tail lesions or tail self-amputations. The median survivals for saline- and AAV9/miniMECP2-miRARE-treated KO mice are 9.6 and 15.0 weeks (p<0.02, Gehan-Breslow-Wilcoxon test). Compare to lower doses shown in FIG. 9. FIG. 4B is a graph depicting that none of the treatments significantly affected KO weight. n per group in FIG. 4B: WT, 0 vg (20); KO, 0 vg (18); KO, $1 \times 10^{12}$ vg AAV9/MECP2 (12); KO, $1 \times 10^{12}$ vg AAV9/miniMECP2 (12); and KO, $1 \times 10^{12}$ vg AAV9/miniMECP2-miRARE (12). FIG. 4A and FIG. 4B depict that the same WT control data appears in FIG. 3 as these mice were treated in parallel. FIG. 4C is a plot depicting that the frequency of achieving severe gait (score=2) among saline-, AAV9/MECP2-, AAV9/miniMECP2-, and AAV9/miniMECP2-miRARE-treated mice were 28%, 50%, 33%, and 17%. $1 \times 10^{12}$ vg was administered per mouse. Black bars indicate the mean age of onset for severe clasping. Each data point represents 1 mouse. The fraction of mice (subset versus entire group) is listed for each treatment group. AAV9/miniMECP2-miRARE-treated mice developing severe gait (n=2 out of 12) did so 4-5 weeks after other groups. Although this delay is significantly different, the number of data points are too few to draw firm conclusions. Although FIG. 3D and FIG. 4C show the same type of data, FIG. 4C is plotted in a different format. In general, Kaplan-Meier plots are the clearest way to visually communicate age-of-onset data (see FIG. 3D), but these plots lend themselves to the intuitive assumption that all mice retaining normal gait live for the entire time period specified on the X-axis. This is true for WT mice (FIG. 3D) but not for KO mice (FIG. 4C). Importantly, few AAV9/miniMECP2-miRARE-treated KO mice developed severe gait, despite having an extended survival. FIG. 4D is a graph depicting that a high dose ($1 \times 10^{12}$ vg/mouse) of AAV9/miniMECP2-miRARE yields a trend in improved initial motor coordination KO mice (versus saline; Trial 1, Day 1). AAV9/miniMECP2-miRARE did not improve motor learning across trials. n=30, 29, and 9 for saline-treated WT, saline-treated KO, and AAV9/miniMECP2-miRARE-treated KO groups. FIG. 4E is a graph depicting that lesions were observed across treatment groups. Due to small group sizes, it is unclear if miRARE decreases the risk of lesions among virus-treated mice. (FIGS. 4B-4D) Data are mean±SEMs.

FIG. 6A-B shows number of targets shared between pairs of 3' UTRs. FIG. 6A and FIG. 6B are tables that depicts the number of shared targets that are indicated for randomly selected human genes (FIG. 6A) and for a curated list of human genes (FIG. 6B). In FIG. 6A the 3' UTR ensemble transcript length ranges from 224 bp to 2382 bp. In FIG. 6B the 3' UTRs for a curated list of genes have many miRNA targets in common. The 3' UTR ensemble transcript length ranges from 1960 bp to 8794 bp.

FIG. 7A and FIG. 7B are tables depicting that shared annotated targets are more densely packed among the 3' UTRs of genes mediating intellectual disability. (FIG. 6A and FIG. 6B) The number of shared targets (See FIG. 6A-B) was divided by the length of the 3' UTR ensemble transcript for the gene listed in the column header and then multiplied by 100 to yield the number of shared targets for a 100 bp length of UTR sequence. Accommodation of up to 22 targets within a 100 bp sequence can be possible if an individual seed match can bind multiple unique miRNAs with similar or identical seed sequences. Only human sequences were analyzed.

FIG. 8A is a graph depicting that $1 \times 10^{11}$ vg/mouse of PHP.B/miniMECP2 causes weight loss in treated WT mice (*p≤ 0.05). In contrast, PHP.B/EGFP and PHP.B/miniMECP2-miRARE were well-tolerated. FIG. 8B is a graph depicting that PHP.B/miniMECP2 increases severity scores in treated WT mice (*p<0.05). In contrast, PHP.B/EGFP and PHP.B/miniMECP2-miRARE were well-tolerated. The same legend applies for FIG. 8A and FIG. 8B. Four PHP.B/miniMECP2- and 3 PHP.B/miniMECP2-miRARE-treated mice were perfused at 3-4 weeks post-injection for immunofluorescence analyses. FIG. 8C is a graph depicting that none of the PHP.B/EGFP-treated mice surviving up to 23 weeks of age (end of study) developed severely abnormal gait (score=2). In comparison, 78% of PHP.B/miniMECP2-treated mice and 33% of PHP.B/miniMECP2-miRARE-treated mice developed severely abnormal gait. FIG. 8D is a graph depicting that none of the PHP.B/EGFP-treated mice developed severe clasping (score=2) by the end of the study. MiRARE may decrease the frequency and delay the age of onset of severe clasping among virus-treated WT mice. (FIG. 8A and FIG. 8B) Data are means±SEMs. The same legend applies for FIG. 8A-FIG. 8D; however, mice perfused at 3-4 weeks post-injection were excluded from FIG. 8C-FIG. 8D. For FIG. 8C and FIG. 8D*p<0.05 using Gehan-Breslow-Wilcoxon test, which can be used to evaluate significance for Kaplan-Meier plots.

DETAILED DESCRIPTION

Figure 1B:

The present disclosure provides, inter alia, isolated polynucleotides, recombinant adeno-associated virus (rAAV) vectors, and rAAV viral vectors comprising transgene nucleic acid molecules comprising nucleic acid sequences encoding for MeCP2 and/or MeCP2-derived polypeptides. The present disclosure also provides methods of manufacturing these isolated polynucleotides, rAAV vectors, and rAAV viral vectors, as well as their use to deliver transgenes to treat or prevent a disease or disorder, including diseases associated with loss and/or misfunction of an MECP2 gene.

A risk-driven viral genome design strategy rooted in high-throughput profiling and genome mining was used to rationally develop a compact, synthetic miRNA target panel (miR-Responsive Auto-Regulatory Element, "miRARE") to minimize the possibility of transgene overexpression in the context of RTT gene therapy and other dose-sensitive gene therapy. The insertion of miRARE into a miniMECP2 gene expression cassette greatly improves the safety of miniMECP2 gene transfer without compromising efficacy. Importantly, this built-in regulation system does not require any additional exogenous drug application, and no miRNAs are expressed from the transgene cassette.

One strategy to improve the efficiency of AAV9-mediated gene transfer is to pair the AAV9 capsid with a self-complementary (sc) viral genome. Compared to single-stranded AAV (ssAAV), self-complementary AAV (scAAV) has a smaller viral genome packaging capacity (~2.2 kb) but permits more efficient transduction due to its ability to bypass the rate-limiting second-strand synthesis in host cells. The reduced packaging capacity of scAAV is important for guiding MECP2 viral genome design as the ~1.5 kb MECP2 gene limits the size of 5' and 3' regulatory elements included in the viral genome cassette. A therapeutic miniMECP2 gene (~0.5 kb) frees up additional space within the sc viral genome for inserting novel regulatory elements to improve the therapeutic index of RTT gene therapy.

AAV9/MECP2 and miniMECP2 gene therapies have been shown to extend KO mouse survival. In KO mice dosed at the neonatal age, survival and behavioral benefits have been realized with less pronounced side effects However, when mice are treated at 4-5 weeks old, a time more relevant for human translation, survival benefits have come with significant side effects (including death) and a lack of clear behavioral rescue. Moreover, this lack of clear behavioral rescue (within the context of AAV9-mediated gene transfer) has been observed across both KO and T158M MeCP2-expressing RTT mice treated during adolescence. Because a high intraCSF dose of AAV9/EGFP—but not AAV9/MECP2—is well-tolerated in WT mice, these dose-dependent side effects are most likely directly due to MeCP2 overexpression. After years of iterative, full-factorial assessments of candidate MECP2 vectors, the field is still wrestling with the same dilemma anticipated from MeCP2-overexpression studies dating back 16 years. High doses of MeCP2-encoding vectors may be harmful; low doses may not be effective. Clearly, this persistent dilemma warrants innovative viral genome design strategies that permit efficacy without compromising safety.

Provided herein are compositions and methods for preventing gene overexpression-related toxicity by inserting miRNA targets into the 3' untranslated region (UTR) of viral genomes. Endogenous miRNAs can base-pair with targets in viral genome-encoded messenger RNAs (mRNAs) and ultimately decrease protein expression levels through RNA interference (RNAi). A miRNA target panel is provided that conditionally regulates exogenous genes such as MECP2 in systems such as the CNS. These target panels can buffer against deleterious overexpression of genes and expression cassettes such as miniMECP2, while permitting sufficient transgene expression to exert a therapeutic effect similar to or greater than that of control vectors such as MECP2 or miniMECP2 control vectors. A risk-driven viral genome design strategy rooted in high-throughput profiling and genome mining was used to develop a novel miRNA target panel (named miR-Responsive Autoregulatory Element or "miRARE") for regulating gene and expression cassette expression (e.g. miniMeCP2 expression). A feedback mechanism for negative transgene regulation that is responsive to gene overexpression (e.g. MeCP2 overexpression). Data described herein show that miRARE improves the safety of scAAV9/miniMECP2 gene therapy without compromising efficacy following intracerebrospinal fluid (intraCSF) injection in juvenile mice.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VP1, VP2 and VP3. In some aspects, the AAV refers to the serotype AAV1, AAV2, AAV4, AAV5, AAV6, AAV7, AAV8, AAV9, AAV10, AAV11, AAV12, AAV13, AAVPHP.B, AAVrh74 or AAVrh. 10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74 and AAVrh. 10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22):e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC 001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928. U.S. Pat. No. 9,434,928 also provides the sequences of the capsid proteins and a self-complementary genome. In one aspect, an AAV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus poly A site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein.

The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise, consist essentially of, or consist of a nucleic acid molecule encoding a therapeutic protein (e.g., GAT1) and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

Isolated Polynucleotides Comprising Transgene Sequences

The present disclosure provides isolated polynucleotides comprising at least one transgene nucleic acid molecule.

In some aspects, a transgene nucleic acid molecule can comprise a nucleic acid sequence encoding a MeCP2 polypeptide and/or MeCP2-derived polypeptide, or at least one fragment thereof. In some aspects, a transgene nucleic acid molecule can comprise a nucleic acid sequence encoding a biological equivalent of a MeCP2 polypeptide and/or MeCP2-derived polypeptide. An MeCP2-derived polypeptide can be a polypeptide that has been specifically designed based on a wildtype MeCP2 polypeptide to include only the domains absolutely essential for function. In this way, an MeCP2-derived polypeptide can be smaller than an endogenous, wildtype MeCP2 polypeptide, leading to, amongst other things, increased expression in vivo and the ability to be efficiently packaged into vectors that have inherent size constraints (such as, but not limited to, AAV vectors).

In some aspects, an MeCP2-derived polypeptide can be a human MeCP2 isoform-derived miniMeCP2 polypeptide, hereafter referred to as a "miniMeCP2" polypeptide.

In some aspects, a miniMeCP2 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2, or a fragment thereof. In some aspects, a miniMeCP2 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1, or a fragment thereof.

In some aspects, a nucleic acid sequence encoding a miniMeCP2 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO: 3, SEQ ID NO: 4 or SEQ ID NO: 28. In some aspects, a nucleic acid sequence encoding a miniMeCP2 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 3. In some aspects, a nucleic acid sequence encoding a miniMeCP2 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 28.

In some aspects, the nucleic acid sequence encoding a MeCP2 polypeptide and/or an MeCP2-derived polypeptide can be a codon optimized nucleic acid sequence that encodes for a MeCP2 polypeptide and/or an MeCP2-derived polypeptide. A codon optimized nucleic acid sequence encoding a MeCP2 polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the MeCP2 polypeptide. As used herein, the "wildtype human nucleic acid sequence encoding the MeCP2 polypeptide" refers to the nucleic acid sequence that encodes the MECP2 polypeptide in a human genome.

In some aspects, a codon optimized nucleic acid sequence encoding a MeCP2 polypeptide and/or an MeCP2-derived polypeptide can comprise no donor splice sites. In some aspects, a codon optimized nucleic acid sequence encoding a MeCP2 polypeptide and/or an MeCP2-derived polypeptide can comprise no more than about one, or about two, or about three, or about four, or about five, or about six, or about seven, or about eight, or about nine, or about ten donor splice sites. In some aspects, a codon optimized nucleic acid sequence encoding a MeCP2 polypeptide and/or an MeCP2-derived polypeptide comprises at least one, or at least two, or at least three, or at least four, or at least five, or at least six, or at least seven, or at least eight, or at least nine, or at least ten fewer donor splice sites as compared to the wild-type human nucleic acid sequence encoding the MeCP2 polypeptide and/or an MeCP2-derived polypeptide. Without wishing to be bound by theory, the removal of donor splice sites in the codon optimized nucleic acid sequence can unexpectedly and unpredictably increase expression of the MeCP2 polypeptide and/or an MeCP2-derived polypeptide in vivo, as cryptic splicing is prevented. Moreover, cryptic splicing may vary between different subjects, meaning that the expression level of the MeCP2 polypeptide and/or an MeCP2-derived polypeptide comprising donor splice sites may unpredictably vary between different subjects.

In some aspects, a codon optimized nucleic acid sequence encoding an MeCP2 polypeptide and/or an MeCP2-derived polypeptide can have a GC content that differs from the GC content of the wildtype human nucleic acid sequence encoding the MeCP2 polypeptide. In some aspects, the GC content of a codon optimized nucleic acid sequence encoding a MeCP2 polypeptide and/or an MeCP2-derived polypeptide is more evenly distributed across the entire nucleic acid sequence, as compared to the wildtype human nucleic acid sequence encoding the MeCP2 polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, the codon optimized nucleic acid sequence encoding an MeCP2 polypeptide and/or an MeCP2-derived polypeptide exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding an MeCP2 polypeptide.

In some aspects, an MeCP2 polypeptide and/or an MeCP2-derived polypeptide can further comprise a protein tag. Without wishing to be bound by theory, the inclusion of a protein tag can allow for the detection and/or visualization of the exogenous MeCP2 polypeptide. As would be appreciated by the skilled artisan, non-limiting examples of protein tags include Myc tags, poly-histidine tags, FLAG-tags, HA-tags, SBP-tags or any other protein tag known in the art. In a non-limiting example, an MeCP2 polypeptide and/or an MeCP2-derived polypeptide can further comprise a Myc tag. In some aspects, a Myc tag comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 5.

Accordingly, in some aspects, a nucleic acid sequence encoding an MeCP2 polypeptide and/or an MeCP2-derived polypeptide can further comprise a nucleic acid sequence encoding a myc tag. In some aspects, a nucleic acid sequence encoding a myc tag comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO: 6.

Isolated Polynucleotides Encoding a Regulatory Sequence

The present disclosure provides isolated polynucleotides comprising at least one regulatory sequence.

In some aspects, a regulatory sequence can comprise, consist essentially of, or consist of at least one miRNA binding site. An "miRNA binding site" is a polynucleotide sequence having sufficient complementarity to the sequence of a miRNA to ensure annealing of a miRNA of interest to the polynucleotide and the subsequent downregulation of the transgene.

In some aspects, an miRNA binding site comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in any one of SEQ ID NOs: 7, 8, 9, 10, 11, and 12, as put forth in Table 1.

TABLE 1

| Sequence of miRNA binding site | SEQ ID NO: |
|---|---|
| CCAAAGA | 7 |
| ACTTGAA | 8 |
| ATGTGAA | 9 |
| AGCACAA | 10 |
| CTGTGAA | 11 |
| CTACCTCA | 12 |

In some aspects, a regulatory sequence can comprise, consist essentially of, or consist of at least two, or at least three, or at least four or at least five, or at least six, or at least seven, or at least eight, or at least nine, or at least ten miRNA binding sites. In some aspects, a regulatory sequence can comprise, consist of, or consist essentially of each of the miRNA binding sites put forth in SEQ ID NOs: 7, 8, 9, 10, 11, and 12. Accordingly, in some aspects, a regulatory sequence can comprise one or more of SEQ ID NO: 7, SEQ ID NO: 8, SEQ ID NO: 9, SEQ ID NO: 10, SEQ ID NO: 11 and SEQ ID NO: 12, or any combination thereof. In some aspects, a regulatory sequence can comprise each of SEQ ID NO: 7, SEQ ID NO: 8, SEQ ID NO: 9, SEQ ID NO: 10, SEQ ID NO: 11 and SEQ ID NO: 12.

In some aspects, a miRNA binding site can be located adjacent to a flanking sequence. A flanking sequence can occur before (5') an miRNA binding site, after (3') an miRNA binding site, or both before and after an miRNA binding site. A flanking sequence can comprise about 5 to about 35 nucleotides or about 9 to about 29 nucleotides.

Provided herein is a regulatory sequence referred to as a "Reg2 sequence" or a "Reg2 panel". In some aspects, a Reg2 sequence can comprise 6 binding sites that are predicted to bind let-7-5p miRNAs (or miR-98-5p), miR-218-5p, miR-9-5p, miR-26-5p, miR-23-3p, miR-27-3p, or other miRNAs with similar seed sequences to miRNAs described herein.

In some aspects, a Reg 2 sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO: 13. SEQ ID NO: 13 is shown below, with the miRNA binding sites of SEQ ID Nos: 7-12 underlined. The portions of SEQ ID NO: 13 that are not underlined are flanking sequences:

(SEQ ID NO: 13)
CTGTTCTAGCCCCCAAAGAGTTTTCTGTGCTTGCTTTTGAAACTTGAAGT

CTTGAAAACCAAAGACATAGATGTGAAAATTTTAGGCAGTGTAAGCTGAT

AGCACAAGTTCTGGCGACTCACAATTATGCTGTGAATTTTACAAAAAGAA

GCAGTAATCTACCTCAGCCGATAAC.

In some aspects, a Reg2 sequence comprises, consists essentially of, or consists of a nucleic acid sequence comprising one or more of SEQ ID NO: 7, 8, 9, 10, 11 and 12, or any combination thereof. In some aspects, the flanking sequences are not limited to those as shown in SEQ ID NO:8, can vary greatly, and are not particularly limited. Therefore, in an embodiment, a Reg2 sequence comprises a polypeptide having one or more of SEQ ID NO: 7-12 separated by (i.e., occurring before (5') and after (3') each binding site) about 9, 10, 11, 12, 13, 14, 15, 16, 17, 18, 19, 20, 21, 22, 23, 24, 25, 26, 27, 28, 29, or more flanking nucleotides, whose sequence is not particularly limited. In some aspects, a Reg2 sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in any one of SEQ ID NO:15, 16, 17, 18, 19, and 20. In an embodiment, a Reg2 sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the flanking sequences shown in SEQ ID NO: 8 (i.e., the non-underlined polynucleotides shown above).

In some aspects, a regulatory sequence comprises, consists essentially of, or consists of a RDH1pA element. An RDH1pA element is a synthetic 3' UTR containing 110 bp of the highly conserved MECP2 distal polyadenylation signal and an upstream miRNA-binding panel containing sites for three additional miRNA targets predicted or shown to be endogenous to the MECP2 3' UTR: miR-19, miR-22, and miR-132. In some aspects, an RDH1pA element sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 14.

In some aspects, an RDH1pA element with SEQ ID NO: 14 can be separated into two component parts: a first component, hereafter referred to as "RDH1pA miRNA binding sites sequence"; and a second component, herein referred to as an "MECP2 downstream polyA (pA) sequence".

In some aspects, an RDH1pA miRNA binding sites sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 15.

In some aspects, an MECP2 downstream polyA (pA) sequence comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 16.

In some aspects, a regulatory sequence can comprise both a Reg2 sequence and a RDH1pA element. In some aspects, a Reg2 sequence can be located between the first component (RDH1pA miRNA binding sites sequence) of the RDH1pA element and the second component (MECP2 downstream polyA (pA) sequence) of the RDH1pA. The Reg2 sequence can be immediately adjacent to either or both of the RDH1pA element components, or can be separated from either or both of the RDH1pA element components by about 2-10 nucleotides.

Accordingly, a regulatory sequence can comprise, in the 5' to 3' direction, SEQ ID NO: 15, followed by SEQ ID NO: 13, followed by SEQ ID NO: 16. Such a regulatory sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 17.

AAV Vectors

In some aspects, the isolated polynucleotides comprising at least one transgene nucleic acid molecule described herein can be a recombinant AAV (rAAV) vector.

As used herein, the term "vector" refers to a nucleic acid comprising, consisting essentially of, or consisting of an intact replicon such that the vector may be replicated when placed within a cell, for example by a process of transfection, infection, or transformation. It is understood in the art that once inside a cell, a vector may replicate as an extra-chromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

An "rAAV vector" as used herein refers to a vector comprising, consisting essentially of, or consisting of one or more transgene nucleic acid molecules and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing rAAV vectors may also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one regulatory sequence. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one poly A sequence.

In some aspects, an rAAV vector can comprise a first AAV ITR sequence, a promoter sequence, a transgene nucleic acid molecule, a regulatory sequence and a second AAV ITR sequence. In some aspects, an rAAV vector can comprise, in the 5' to 3' direction, a first AAV ITR sequence, a promoter sequence, a transgene nucleic acid molecule, a regulatory sequence and a second AAV ITR sequence.

In some aspects, an rAAV vector can comprise more than one transgene nucleic acid molecule. In some aspects, an rAAV vector can comprise at least two transgene nucleic acid molecules, such that the rAAV vector comprises a first transgene nucleic acid molecule and an at least second transgene nucleic acid molecule. In some aspects, the first and the at least second transgene nucleic acid molecule can comprise the same nucleic acid sequence. In some aspects, the first and the at least second transgene nucleic acid molecules can comprise different nucleic acid sequences. In some aspects, the first and the at least second transgene nucleic acid sequences can be adjacent to each other.

In some aspects, an rAAV vector can comprise more than one promoter sequence. In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer. The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a regulatory sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a regulatory sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a regulatory sequence, and a second AAV ITR sequence.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence or an AAVrh. 10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh. 10 ITR sequence.

In some aspects, an AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NOs: 18, 19 or 30.

In some aspects, an AAV ITR can comprise consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NOs: 20 or 21.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 20.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 19 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 21.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 21.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 19 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 20.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 30 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 20.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 30 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 21.

Promoter Sequence and Enhancers

The term "promoter" and "promoter sequence" as used herein means a control sequence that is a region of a polynucleotide sequence at which the initiation and rate of transcription of a coding sequence, such as a gene or a transgene, are controlled. Promoters may be constitutive, inducible, repressible, or tissue-specific, for example. Promoters may contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, an H1 promoter, a ubiquitous chicken β-actin hybrid (CBh) promoter, a small nuclear RNA (U1a or U1b) promoter, an MECP2 promoter, an MeP426 promoter, a human variant of the MeP426 promoter, a minimal MECP2 promoter, a VMD2 promoter, an mRho promoter, or an EF1 promoter.

Additional non-limiting exemplary promoters provided herein include, but are not limited to EF1a, Ubc, human β-actin, CAG, TRE, Ac5, Polyhedrin, CaMKIIa, Gall, TEF1, GDS, ADH1, Ubi, and α-1-antitrypsin (hAAT). It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters. In some aspects, the promoter is used together with at least one enhancer to increase the transcription efficiency. Non-limiting examples of enhancers include an interstitial retinoid-binding protein (IRBP) enhancer, an RSV enhancer or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a β-actin promoter sequence, a phosphoglycerol kinase (PGK) promoter sequence, a U6 promoter sequence, an H1 promoter sequence, a ubiquitous chicken β-actin hybrid (CBh) promoter sequence, a small nuclear RNA (U1a or U1b) promoter sequence, an MECP2 promoter sequence, an MeP426 promoter sequence, a minimal MECP2 promoter sequence, a VMD2 promoter sequence, an mRho promoter sequence, an EFI promoter sequence, an EF1a promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gall promoter sequence, a TEF1 promoter sequence, a GDS promoter sequence, an ADH1 promoter sequence, a Ubi promoter sequence, a MeP426 promoter, or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) or synthetic techniques such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of an MeP426 promoter sequence. A MeP426 promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 22.

In some aspects, a promoter sequence can comprise, consist essentially of, or consist of a JeT promoter sequence. A JeT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 23.

In some aspects, a promoter sequence can comprise, consist essentially of, or consist of a MeP229 promoter sequence. A MeP229 promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 24.

In some aspects, a promoter sequence can comprise, consist essentially of, or consist of a CBh promoter sequence. A CBh promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 25.

Transgene Nucleic Acid Molecules

Transgene nucleic acid molecules can comprise, consist essentially of, or consist of any of the transgene nucleic acid molecules described above under the heading "isolated polynucleotides comprising transgene sequences".

In some aspects, a transgene nucleic acid molecule present in an rAAV vector can be under transcriptional control of a promoter sequence also present in the same rAAV vector.

Regulatory Sequences

Regulatory can comprise, consist essentially of, or consist of any of the sequences described above under the heading "isolated polynucleotides encoding a regulatory sequence".

Poly A Sequences

In some aspects, a polyadenylation (polyA) sequence can comprise any polyA sequence known in the art. Non-limiting examples of polyA sequences include, but are not limited to, an MECP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

Thus, a poly A sequence can comprise, consist essentially of, or consist of an MeCP2 poly A sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

In some aspects, an MECP2 polyA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 16.

In some aspects, a polyA sequence can comprise, consist essentially of, or consist of an SV40 pA sequence. In some aspects, an SV40 pA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NO: 26.

In some aspects, an rAAV vector of the present disclosure can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NO: 27 or SEQ ID NO: 29.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a prokaryotic promoter.

Origin of Replication Sequence

In some aspects, an origin of replication sequence can comprise, consist essentially of, or consist of any origin of replication sequence known in the art. The origin of replication sequence can be a bacterial origin of replication sequence, thereby allowing the rAAV vector comprising said bacterial origin of replication sequence to be produced, propagated and maintained in bacteria, using methods standard in the art.

Antibiotic Resistance Genes

In some aspects, rAAV vectors and/or rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

AAV Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

An "AAV virion" or "AAV viral particle" or "AAV viral vector" or "rAAV viral vector" or "AAV vector particle" or "AAV particle" refers to a viral particle composed of at least one AAV capsid protein and an encapsidated polynucleotide rAAV vector. Thus, production of an rAAV viral vector necessarily includes production of an rAAV vector, as such a vector is contained within an rAAV vector.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1: VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

The present disclosure provides an rAAV viral vector comprising: a) any of the rAAV vectors described herein; and b) an AAV capsid protein.

An AAV capsid protein can be any AAV capsid protein known in the art. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh. 10 capsid protein.

Alternative rAAV Vector and rAAV Viral Vector Embodiments

1. An rAAV vector, comprising, in the 5' to 3' direction
a) a first AAV ITR sequence;
b) a promoter sequence;
c) a transgene nucleic acid molecule, wherein the transgene nucleic acid molecule comprises a nucleic acid sequence encoding for an MeCP2 polypeptide and/or MeCP2-derived polypeptide;
d) a regulatory sequence; and
e) a second AAV ITR sequence.

2. The rAAV vector of embodiment 1, wherein transgene nucleic acid molecule comprises a nucleic acid sequence encoding for an MeCP2-derived polypeptide.

3. The vector of embodiment 2, wherein the MeCP2-derived polypeptide is a miniMECP2 polypeptide.

4. The vector of embodiment 3, wherein the miniMeCP2 polypeptide comprises the amino acid sequence set forth in SEQ ID NO: 1 or SEQ ID NO:2.

5. The vector of embodiment 4, wherein the miniMeCP2 polypeptide comprises the amino acid sequence set forth in SEQ ID NO: 1.

6. The vector of embodiment 4, wherein the miniMeCP2 polypeptide comprises the amino acid sequence set forth in SEQ ID NO: 2.

7. The rAAV vector of any one of the preceding embodiments, wherein the nucleic acid sequence encoding for an MeCP2 polypeptide and/or MeCP2-derived polypeptide comprises the nucleic acid sequence set forth in SEQ ID NO: 3, SEQ ID NO: 4 or SEQ ID NO: 28.

8. The rAAV vector of any one of the preceding embodiments, wherein the nucleic acid sequence encoding for an MeCP2 polypeptide and/or MeCP2-derived polypeptide comprises the nucleic acid sequence set forth in SEQ ID NO: 3.

9. The rAAV vector of any one of the preceding embodiments, wherein the nucleic acid sequence encoding for an MeCP2 polypeptide and/or MeCP2-derived polypeptide comprises the nucleic acid sequence set forth in SEQ ID NO: 4.

10. The rAAV vector of any one of the preceding embodiments, wherein the nucleic acid sequence encoding for an MeCP2 polypeptide and/or MeCP2-derived polypeptide comprises the nucleic acid sequence set forth in SEQ ID NO: 28.

11. The rAAV vector of any one of the preceding embodiments, wherein the first AAV ITR sequence comprises the nucleic acid sequence set forth in SEQ ID NO: 18.

12. The rAAV vector of any one of the preceding embodiments, wherein the first AAV ITR sequence comprises the nucleic acid sequence set forth in SEQ ID NO: 19.

13. The rAAV vector of any one of the preceding embodiments, wherein the first AAV ITR sequences comprises the nucleic acid sequence set forth in SEQ ID NO: 30.

14. The rAAV vector of any one of the preceding embodiments, wherein the second AAV ITR sequence comprises the nucleic acid sequence set forth in SEQ ID NO: 20.

15. The rAAV vector of any one of the preceding embodiments, wherein the second AAV ITR sequence comprises the nucleic acid sequence set forth in SEQ ID NO: 21.

16. The rAAV vector of any one of the preceding embodiments, wherein the promoter sequence comprises a MeP426 promoter sequence.

17. The rAAV vector of embodiment 15, wherein the MeP426 promoter sequence comprises the nucleic acid sequence set forth in SEQ ID NO: 22.

18. The rAAV vector of any one of the preceding embodiments, wherein the regulatory sequence comprises one or more miRNA binding sites.

19. The rAAV vector of embodiment 17, wherein the one or more miRNA binding sites comprise an miR-9-5p miRNA binding site, a miR-26b-5p miRNA binding site, a miR-23a-3p miRNA binding site, a miR-218-5p miRNA binding site, a miR-27a-3p miRNA binding site, a let-7e-5p miRNA binding site, a miR-98-5p miRNA binding site, a let-7d-5p miRNA binding site, a let-7g-5p miRNA binding site, a miR-218-5p miRNA binding site or any combination thereof.

20. The rAAV vector of any of the preceding embodiments, wherein the regulatory sequence comprises one or more of the nucleic acid sequences set forth in SEQ ID NOs: 7, 8, 9, 10, 11, and 12.

21. The rAAV vector of any of the preceding embodiments, wherein the regulatory sequence comprises two or more of the nucleic acid sequences set forth in SEQ ID NOs: 7, 8, 9, 10, 11, and 12.

22. The rAAV vector of any of the preceding embodiments, wherein the regulatory sequence comprises three or more of the nucleic acid sequences set forth in SEQ ID NOs: 7, 8, 9, 10, 11, and 12.

23. The rAAV vector of any of the preceding embodiments, wherein the regulatory sequence comprises four or more of the nucleic acid sequences set forth in SEQ ID NOs: 7, 8, 9, 10, 11, and 12.

24. The rAAV vector of any of the preceding embodiments, wherein the regulatory sequence comprises five or more of the nucleic acid sequences set forth in SEQ ID NOs: 7, 8, 9, 10, 11, and 12.

25. The rAAV vector of any of the preceding embodiments, wherein the regulatory sequence comprises each of the nucleic acid sequences set forth in SEQ ID NOs: 7, 8, 9, 10, 11, and 12.

26. The rAAV vector of any of the preceding embodiments, wherein the regulatory sequence comprises the nucleic acid sequence set forth in SEQ ID NO: 13.

27. The rAAV vector of any of the preceding embodiments, wherein the regulatory sequence comprises the nucleic acid sequence set forth in SEQ ID NO: 14.

28. The rAAV vector of any of the preceding embodiments, wherein the regulatory sequence comprises the nucleic acid sequence set forth in SEQ ID NO: 15

29. The rAAV vector of any of the preceding embodiments, wherein the regulatory sequence comprises the nucleic acid sequence set forth in SEQ ID NO: 16.

30. The rAAV vector of any of the preceding embodiments, wherein the regulatory sequence comprises, in the 5' to 3' direction,
i) the nucleic acid sequence set forth in SEQ ID NO: 15;
ii) the nucleic acid sequence set forth in SEQ ID NO: 13; and
iii) the nucleic acid sequence set forth in SEQ ID NO: 16.

31. The rAAV vector of any of the preceding embodiments, wherein the regulatory sequence comprises the nucleic acid sequence set forth in SEQ ID NO: 17.

32. An rAAV vector, comprising, in the 5' to 3' direction
a) a first AAV ITR sequence comprising the nucleic acid sequence set forth in SEQ ID NO: 18, SEQ ID NO: 19 or SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1 or SEQ ID NO: 2;
d) a regulatory sequence comprising the nucleic acid sequence set forth in SEQ ID NO: 17; and
e) a second AAV ITR sequence comprising the nucleic acid sequence set forth in SEQ ID NO: 20 or SEQ ID NO: 21.

33. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 20.

34. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 21.

35. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 20.

36. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 21.

37. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 20.

38. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 17; and
e) a second AAV ITR sequence comprising the nucleic acid sequence set forth in SEQ ID NO: 21.

39. An rAAV vector, comprising, in the 5' to 3' direction
a) a first AAV ITR sequence comprising the nucleic acid sequence set forth in SEQ ID NO: 18, SEQ ID NO: 19 or SEQ ID NO: 30;

b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1 or SEQ ID NO: 2;
d) a regulatory sequence comprising the nucleic acid sequence set forth in SEQ ID NO: 13; and
e) a second AAV ITR sequence comprising the nucleic acid sequence set forth in SEQ ID NO: 20 or SEQ ID NO: 21.

40. An rAAV vector, comprising, in the 5' to 3' direction
a) a first AAV ITR sequence comprising the nucleic acid sequence set forth in SEQ
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 20.

41. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 21.

42. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 20.

43. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 21.

44. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 20.

45. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the MeCP2 polypeptide and/or MeCP2-derived polypeptide comprises the amino acid sequence set forth in SEQ ID NO: 1;
d) a regulatory sequence comprising the nucleic acid sequence set forth in SEQ ID NO: 13; and
e) a second AAV ITR sequence comprising the nucleic acid sequence set forth in SEQ ID NO: 21.

46. An rAAV vector, comprising, in the 5' to 3' direction
a) a first AAV ITR sequence comprising the nucleic acid sequence set forth in SEQ ID NO: 18, SEQ ID NO: 19 or SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence set forth in SEQ ID NO: 3, SEQ ID NO: 4 or SEQ ID NO: 28;
d) a regulatory sequence comprising the nucleic acid sequence set forth in SEQ ID NO: 17; and
e) a second AAV ITR sequence comprising the nucleic acid sequence set forth in SEQ ID NO: 20 or SEQ ID NO: 21.

47. An rAAV vector, comprising, in the 5' to 3' direction
a) a first AAV ITR sequence comprising the nucleic acid sequence set forth in SEQ
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 20.

48. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 21.

49. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 20.

50. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 21.

51. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 20.

52. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 17; and
e) a second AAV ITR sequence comprising the nucleic acid sequence set forth in SEQ ID NO: 21.

53. An rAAV vector, comprising, in the 5' to 3' direction
a) a first AAV ITR sequence comprising the nucleic acid sequence set forth in SEQ ID NO: 18, SEQ ID NO: 19 or SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence set forth in SEQ ID NO: 3, SEQ ID NO: 4, or SEQ ID NO: 28;
d) a regulatory sequence comprising the nucleic acid sequence set forth in SEQ ID NO: 13; and
e) a second AAV ITR sequence comprising the nucleic acid sequence set forth in SEQ ID NO: 20 or SEQ ID NO: 21.

54. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 20.

55. An rAAV vector, comprising, in the 5' to 3' direction
a) a first AAV ITR sequence comprising the nucleic acid sequence set forth in SEQ ID NO: 18;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 21.

56. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 20.

57. An rAAV vector, comprising, in the 5' to 3' direction
a) a first AAV ITR sequence comprising the nucleic acid sequence set forth in SEQ ID NO: 19;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 21.

58. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 20.

59. An rAAV vector, comprising, in the 5' to 3' direction
a) a first AAV ITR sequence comprising the nucleic acid sequence set forth in SEQ ID NO: 30;
b) a promoter sequence comprising an MeP426 promoter sequence, wherein the MeP426 comprises the nucleic acid sequence set forth in SEQ ID NO: 22;
c) a transgene nucleic acid molecule, wherein the transgene nucleic acid molecule comprises a nucleic acid sequence encoding for an MeCP2 polypeptide and/or MeCP2-derived polypeptide, wherein the nucleic acid sequence encoding for an MeCP2 polypeptide and/or MeCP2-derived polypeptide comprises the nucleic acid sequence of SEQ ID NO: 3;
d) a regulatory sequence comprising the nucleic acid sequence set forth in SEQ ID NO: 13; and
e) a second AAV ITR sequence comprising the nucleic acid sequence set forth in SEQ ID NO: 21.

60. An rAAV vector of any one of the preceding embodiments, wherein the rAAV vector comprises the nucleic acid sequence of SEQ ID NO: 27.

61. An rAAV vector of any one of the preceding embodiments, wherein the rAAV vector comprises the nucleic acid sequence of SEQ ID NO: 29.

62. An rAAV viral vector comprising:
a) an rAAV vector of any one of the preceding embodiments; and
b) an AAV capsid protein.

63. The rAAV viral vector of embodiment 62, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

64. The rAAV viral vector of embodiment 62, wherein the AAV capsid protein is an AAV1 capsid protein.
65. The rAAV viral vector of embodiment 62, wherein the AAV capsid protein is an AAV2 capsid protein.
66. The rAAV viral vector of embodiment 62, wherein the AAV capsid protein is an AAV3 capsid protein.
67. The rAAV viral vector of embodiment 62, wherein the AAV capsid protein is an AAV4 capsid protein.
68. The rAAV viral vector of embodiment 62, wherein the AAV capsid protein is an AAV5 capsid protein.
69. The rAAV viral vector of embodiment 62, wherein the AAV capsid protein is an AAV6 capsid protein.
70. The rAAV viral vector of embodiment 62, wherein the AAV capsid protein is an AAV7 capsid protein.
71. The rAAV viral vector of embodiment 62, wherein the AAV capsid protein is an AAV8 capsid protein.
72. The rAAV viral vector of embodiment 62, wherein the AAV capsid protein is an AAV9 capsid protein.
73. The rAAV viral vector of embodiment 62, wherein the AAV capsid protein is an AAV10 capsid protein.
74. The rAAV viral vector of embodiment 62, wherein the AAV capsid protein is an AAV11 capsid protein.
75. The rAAV viral vector of embodiment 62, wherein the AAV capsid protein is an AAV12 capsid protein.

76. The rAAV viral vector of embodiment 62, wherein the AAV capsid protein is an AAV13 capsid protein.

77. The rAAV viral vector of embodiment 62, wherein the AAV capsid protein is an AAVPHP.B capsid protein.

78. The rAAV viral vector of embodiment 62, wherein the AAV capsid protein is an AAVrh74 capsid protein.

79. The rAAV viral vector of embodiment 62, wherein the AAV capsid protein is an AAVrh. 10 capsid protein.

80. An rAAV vector comprising a regulatory sequence, wherein the regulatory sequence comprises one or more miRNA binding sites.

81. The rAAV vector of embodiment 70, wherein the one or more miRNA binding sites comprise an miR-9-5p miRNA binding site, a miR-26b-5p miRNA binding site, a miR-23a-3p miRNA binding site, a miR-218-5p miRNA binding site, a miR-27a-3p miRNA binding site, a let-7e-5p miRNA binding site, a miR-98-5p miRNA binding site, a let-7d-5p miRNA binding site, a let-7g-5p miRNA binding site, a miR-218-5p miRNA binding site or any combination thereof.

82. The rAAV vector of any of embodiments 80-81, wherein the regulatory sequence comprises one or more of the nucleic acid sequences set forth in SEQ ID NOs: 7, 8, 9, 10, 11, and 12.

83. The rAAV vector of any of embodiments 80-82, wherein the regulatory sequence comprises two or more of the nucleic acid sequences set forth in SEQ ID NOs: 7, 8, 9, 10, 11, and 12.

84. The rAAV vector of any of embodiments 80-83, wherein the regulatory sequence comprises three or more of the nucleic acid sequences set forth in SEQ ID NOs: 7, 8, 9, 10, 11, and 12.

85. The rAAV vector of any of embodiments 80-84, wherein the regulatory sequence comprises four or more of the nucleic acid sequences set forth in SEQ ID NOs: 7, 8, 9, 10, 11, and 12.

86. The rAAV vector of any of embodiments 80-85, wherein the regulatory sequence comprises five or more of the nucleic acid sequences set forth in SEQ ID NOs: 7, 8, 9, 10, 11, and 12.

87. The rAAV vector of any of embodiments 80-86, wherein the regulatory sequence comprises each of the nucleic acid sequences set forth in SEQ ID NOs: 7, 8, 9, 10, 11, and 12.

88. The rAAV vector of any of embodiments 80-87, wherein the regulatory sequence comprises the nucleic acid sequence set forth in SEQ ID NO: 13.

89. The rAAV vector of any of embodiments 80-88, wherein the regulatory sequence comprises the nucleic acid sequence set forth in SEQ ID NO: 14.

90. The rAAV vector of any of embodiments 80-89, wherein the regulatory sequence comprises the nucleic acid sequence set forth in SEQ ID NO: 15

91. The rAAV vector of any of embodiments 80-90, wherein the regulatory sequence comprises the nucleic acid sequence set forth in SEQ ID NO: 16.

92. The rAAV vector of any of embodiments 80-91, wherein the regulatory sequence comprises, in the 5' to 3' direction,
   i) the nucleic acid sequence set forth in SEQ ID NO: 15;
   ii) the nucleic acid sequence set forth in SEQ ID NO: 13; and
   iii) the nucleic acid sequence set forth in SEQ ID NO: 16.

93. The rAAV vector of any of embodiments 80-92, wherein the regulatory sequence comprises the nucleic acid sequence set forth in SEQ ID NO: 17.

94. An rAAV viral vector comprising:
   a) an rAAV vector of any of embodiments 80-93; and
   b) an AAV capsid protein.

Compositions and Pharmaceutical Compositions

The present disclosure provides compositions comprising any of the isolated polynucleotides, rAAV vectors, and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, may be formulated by any methods known or developed in the art of pharmacology, which include but are not limited to contacting the active ingredients (e.g., viral particles or recombinant vectors) with an excipient and/or additive and/or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations of the invention can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additive. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term "cryoprotectant" refers to an agent capable of reducing or eliminating damage to a substance during freezing. Non-limiting examples of cryoprotectants include sucrose, trehalose, lactose, glycerol, dextrose, raffinose and/or mannitol.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

In some aspects, a pharmaceutical composition of the present disclosure can comprise phosphate-buffered saline (PBS), D-sorbitol or any combination thereof.

In some aspects, a pharmaceutical composition can comprise PBS, wherein the PBS is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

Thus, the present disclosure provides a pharmaceutical composition comprising an rAAV vector and/or rAAV viral vector of the present disclosure in a 350 mM phosphate-buffered saline solution comprising D-sorbitol at a concentration of 5%.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

This disclosure provides methods of preventing or treating a disorder, comprising, consisting essentially of, or consisting of administering to a subject a therapeutically effective amount of any one of the rAAV vectors, rAAV viral vectors, compositions and/or pharmaceutical compositions disclosed herein.

In some aspects, the disease can be a genetic disorder involving the MECP2 gene. A genetic disorder involving the MECP2 gene can be MECP2 deficiency.

A genetic disorder involving the MECP2 gene can be Rett syndrome.

In some aspects, a disease can be a disease that is characterized by the loss-of-function of at least one copy of the MECP2 gene in the genome of a subject. In some aspects, a disease can be a disease that is characterized by a decrease in function of at least one copy of the MECP2 gene in the genome of a subject. In some aspects, a disease can be a disease that is characterized by at least one mutation in at least one mutation in at least one copy of the MECP2 gene in the genome of the subject.

A mutation in a MECP2 gene can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, the products of proteomic cleavage.

In some aspects, a disease can be a disease that is characterized by a decrease in expression of the MECP2 gene in a subject as compared to a control subject that does not have the disease. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the amount of MeCP2 in a subject as compared to a control subject that does not have the disease. In some aspects, the decrease in the amount of MeCP2 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the activity of MeCP2 in a subject as compared to a control subject that does not have the disease. In some aspects, the decrease in the activity of MeCP2 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

Methods of treatment can alleviate one or more symptoms of Rett syndrome. In an embodiment, delivery of compositions described herein can prevent or delay development of detectable symptoms, if administered to a subject carrying a mutation in the MECP2 gene before symptoms become detectable. Therefore, treatment can be therapeutic or prophylactic. Therapy refers to inhibition or reversal of established symptoms or phenotype. Therapy can also mean delay of onset of symptoms or phenotype. Prophylaxis means inhibiting or preventing development of symptoms in subjects not already displaying overt symptoms. Subjects not displaying overt symptoms can be identified early in life as carrying a loss of function mutation in the MECP2 gene by appropriate genetic testing performed before 18 months, 12 months, or 6 months of age.

Symptoms of Rett syndrome include, for example, slowed brain growth (microcephaly) and delayed growth in other parts of the body, loss of normal movement and coordination, loss of communication abilities, abnormal hand movements, unusual eye movements, breathing problems (e.g., breath-holding, abnormally rapid breathing (hyperventilation), forceful exhalation of air or saliva, and swallowing air), irritability and crying, cognitive disabilities, seizures, scoliosis, irregular heartbeat, sleep disturbances, thin, fragile bones prone to factures, small hands and feet that are usually cold, problems with chewing and swallowing, problems with bowel function, and teeth grinding.

The stages of Rett syndrome include, for example, stage I is early onset (usually beginning at between 6 and 18 months of age and can last for a few months or a year). Stage II is rapid deterioration (beginning at about 1 and 4 years of age). Stage III is plateau (usually beginning between the ages of 2 and 10 years and can last for many years). Stage IV is late motor deterioration (usually beginning after the age of 10 and can last for years or decades). Slowed growth of a child's head or other parts of the body. Compositions and methods described herein can be used to treat a patient at any stage of Rett syndrome.

A subject to be treated using the methods, compositions, pharmaceutical compositions, rAAV vectors or rAAV viral vectors of the present disclosure can have any of the diseases and/or symptoms described herein.

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein may be combined with appropriate diagnostic techniques to identify and select patients for the therapy or prevention.

The disclosure provides methods of increasing the level of a protein in a host cell, comprising contacting the host cell with any one of the rAAV viral vectors disclosed herein, wherein the rAAV viral vectors comprises any one of the rAAV vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The disclosure provides methods of introducing a gene of interest to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, or leporid species, as well as other livestock, sport animals, or pets. In some aspects, the subject is a human.

As used herein, "treating" or "treatment" of a disease in a subject refers to (1) inhibiting the disease or arresting its development; or (2) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, "preventing" or "prevention" of a disease refers to preventing the symptoms or disease from occurring in a subject that is predisposed or does not yet display symptoms of the disease.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, the effective amount can be the amount sufficient to result in regaining part or full function of a gene that is deficient in a subject. In some aspects, the effective amount of an rAAV viral vector is the amount sufficient to result in expression of a gene in a subject such that an MeCP2 polypeptide or MeCP2-derived polypeptide is produced. In some aspects, the effective amount is the amount required to increase galactose metabolism in a subject in need thereof. The skilled artisan will be able to determine appropriate amounts depending on these and other factors.

In some aspects, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In some aspects of the methods described herein, the number of viral particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{14}$ to about $10^{15}$, about $5\times10^{11}$ to about $5\times10^{12}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$ or at least about $10^{17}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intranervally, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, intranerve or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna *magna* or via a permanently positioned tube. In some aspects, the rAAV viral vectors of the present disclosure are administered intrathecally.

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some aspects, the rAAV viral vectors of this disclosure show enhanced tropism for brain and cervical spine. In some aspects, the rAAV viral vectors of the disclosure can cross the blood-brain-barrier (BBB).

Methods of Manufacture

A variety of approaches may be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid may be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

Kits

The isolated polynucleotides, rAAV vectors, rAAV viral vectors, compositions, and/or pharmaceutical compositions described herein may be assembled into pharmaceutical or diagnostic or research kits to facilitate their use in therapeutic, diagnostic, or research applications. In some aspects, the kits of the present disclosure include any one of the isolated polynucleotides, rAAV vectors, rAAV viral vectors, compositions, pharmaceutical compositions, host cells, isolated tissues, as described herein.

In some aspects, a kit further comprises instructions for use. Specifically, such kits may include one or more agents described herein, along with instructions describing the intended application and the proper use of these agents. In some aspects, the kit may include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some aspects, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

Further Definitions

Unless the context indicates otherwise, it is specifically intended that the various features of the invention described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure. In each instance herein any of the terms "comprising," "consisting essentially of," and "consisting of" can be replaced with either of the other two terms, while retaining their ordinary meanings. Any single term, single element, single phrase, group of terms, group of phrases, or group of elements described herein can each be specifically excluded from the claims.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, promoters can be operatively linked to the downstream sequences.

The term "encode" as it is applied to polynucleotides and/or nucleic acid sequences refers to a polynucleotide and/or nucleic acid sequence which is said to "encode" a polypeptide if, in its native state or when manipulated by methods well known to those skilled in the art, it can be transcribed to produce the mRNA for the polypeptide and/or a fragment thereof. The antisense strand is the complement of such a nucleic acid, and the encoding sequence can be deduced therefrom.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

EXAMPLES

Materials and Methods for Examples 1-5

Animals: Mice were provided chow and water ad libitum and were housed on a 12-hour light-dark cycle. Animal studies were conducted in accordance with a protocol approved by the Institutional Animal Care and Use Committee at the University of North Carolina (UNC) at Chapel Hill (FIGS. 1A-1C) and the University of Texas Southwestern (UTSW) Medical Center (all other figures). All mice were weaned at P28 (Sinnett, S. E., et al. Mol Ther Methods Clin Dev, 2017. 5: p. 106-115). Mice were housed and evaluated within a barrier facility with the following exception: Mice in FIG. 4D were bred, housed, and evaluated in a conventional facility.

Vectors:
  a) AAV9/CBH-EGFP: a viral vector comprising AAV9 capsid proteins and an rAAV vector comprising a chicken β-actin hybrid (CBh) promoter followed by a nucleic acid encoding an eGFP polypeptide
  b) AAV9/MeP426-hMECP2-myc-RDH1 pA (hereafter referred to as "AAV9/MECP2"): a viral vector comprising AAV9 capsid proteins and an rAAV vector comprising, in the 5' to 3' direction, an MeP426 promoter sequence, a nucleic acid sequence encoding human MeCP2, a nucleic acid sequence encoding a myc tag and a regulatory sequence comprising the nucleic acid sequence set forth in SEQ ID NO: 14.
  c) AAV9-MeP426-miniMECP2-myc-RDH1pA (hereafter referred to as "AAV9/miniMECP2"): a viral vector comprising AAV9 capsid proteins and an rAAV vector comprising, in the 5' to 3' direction, an MeP426 promoter sequence, a nucleic acid sequence encoding a miniMeCP2 polypeptide comprising the amino acid sequence of SEQ ID NO: 1, a nucleic acid sequence encoding a myc tag and a regulatory sequence comprising the nucleic acid sequence set forth in SEQ ID NO: 14.

d) AAV9-MeP426-miniMECP2-myc-miRARE-RDH1pA (hereafter referred to as "AAV9/miniMECP2-miRARE"): a viral vector comprising AAV9 capsid proteins and an rAAV vector comprising, in the 5' to 3' direction, an MeP426 promoter sequence, a nucleic acid sequence encoding a miniMeCP2 polypeptide comprising the amino acid sequence of SEQ ID NO: 1, a nucleic acid sequence encoding a myc tag and a regulatory sequence comprising the nucleic acid sequence set forth in SEQ ID NO: 17.

e) PHP.B/miniMECP2-myc: a viral vector comprising PHP.B capsid proteins and an rAAV vector comprising, in the 5' to 3' direction, an MeP426 promoter sequence, a nucleic acid sequence encoding a miniMECP2-myc polypeptide comprising the amino acid sequence of SEQ ID NO: 1, a nucleic acid sequence encoding a myc tag and a regulatory sequence comprising the nucleic acid sequence set forth in SEQ ID NO: 14.

f) PHP.B/miniMECP2-myc-miRARE: a viral vector comprising PHP.B capsid proteins and an rAAV vector comprising, in the 5' to 3' direction, an MeP426 promoter sequence, a nucleic acid sequence encoding a miniMECP2-myc polypeptide comprising the amino acid sequence of SEQ ID NO: 1, a nucleic acid sequence encoding a myc tag and a regulatory sequence comprising the nucleic acid sequence set forth in SEQ ID NO: 17.

g) PHP.B/CBH-EGFP vectors: a viral vector comprising PHP.B capsid proteins and an rAAV vector comprising a chicken β-actin hybrid (CBh) promoter followed by a nucleic acid encoding an eGFP polypeptide All vectors were produced by UNC Vector Core (Clement, N. and J. C. Grieger. Mol Ther Methods Clin Dev, 2016. 3: p. 16002).

All of the above vectors had self-complementary genomes, and all were prepared in a formulation buffer of 350 mM PBS containing 5% D-sorbitol.

A 6-target miRARE panel was inserted between two sub-components of RDH1 pA. Those 2 subcomponents are a 3-target panel for miR-19, miR-22, and miR-132 and a 110 bp fragment of the conserved distal polyadenylation signal. The sequence for miRARE (Reg2 sequence) is (SEQ ID NO: 8)
5'CTGTTCTAGCCCCCAAAGAGTTTTCTGTGCTTGCTTTTGAAACTTGAA

GTCTTGAAAACCAAAGACATAGATGTGAAATTTTAGGCAGTGTAAGCTG

ATAGCACAAGTTCTGGCGACTCACAATTATGCTGTGAATTTTACAAAAAG

AAGCAGTAATCTACCTCAGCCGATAAC-3'.

Underlined sequences indicate seed matches for miR-9-5p, miR-26-5p miR-23-3p, miR-218-5p, miR-27-3p, and let-7-5p, respectively. Non-underlined portions represent flanking sequences. These targets and flanking sequences meet a number of criteria: (1) The bolded mutation was introduced to create a TIA anchor (Schirle, N. T., et al. Science, 2014. 346(6209): p. 608-13). (2) The spacers between each underlined sequence are within desired ranges for cooperative repression (Grimson, A., et al. Mol Cell, 2007. 27(1): p. 91-105; Saetrom, P., et al. Nucleic Acids Res, 2007. 35(7): p. 2333-42). (3) Most of the targets permit a T9A or T9U (Lewis, B. P., et al. Cell, 2005. 120(1): p. 15-20).

Treatments: Surgical intracisternal or percutaneous IT injections (10 µL) were performed on 4-5 week-old mice. Injection methods well known to those skilled in the art were used with the following exception: carprofen (5 mg/kg) and lidocaine (5 µL, 2% solution) were administered subcutaneously (instead of intraperitoneal Avertin) prior to inhalational isoflurane anesthesia. (Sinnett, S. E., et al. Mol Ther Methods Clin Dev, 2017. 5: p. 106-115; Gray, S. J., et al. Curr Protoc Neurosci, 2011. Chapter 4: p. Unit 4 17). IT injections were performed by personnel blinded to treatment.

RNA Purification: Three mice per group were treated with either saline, $1 \times 10^{12}$ vg AAV9/MECP2, or $1 \times 10^{12}$ vg AAV9/EGFP. Two to three weeks after injection, mice were euthanized with a lethal dose of intraperitoneal Avertin and decapitated. Cervical cord, cerebellum, and medulla were rapidly dissected, frozen on dry ice, and immediately transferred to −80° C. Qiagen miRNeasy Mini kits were used to purify total RNA from thawed, lysed tissue. RNA samples were stored at −80° ° C. until they were shipped on dry ice for screening.

MiRNA Profiling: LC Sciences profiled mouse miRNAs from blinded RNA samples was profiled (microarray part number MRA-1002; miRBase version 21; n=3 mice per group per tissue type with 2 screening replicates) and statistical analyses were performed. Normalized signal was defined as intensities below 500. Significantly increased miRNA expression levels described herein are limited to those having a mean signal intensity exceeding 500.

Bioinformatics: Endogenous targets discussed herein are based on annotations listed in targetscan.org, where Excel files for 21 3' UTRs were downloaded (Release 7.2 Mar. 2018) (Agarwal, V., et al. Elife, 2015. 4). When two 3' UTR sequences were available for a single gene, the most prevalent transcript was selected for analysis. For MECP2, for example, the 8 kb transcript from which a portion of RDH1pA is derived was used for analysis. Targets from downloaded files were merged into a single master file used to create a frequency table. All uniquely annotated targets were considered regardless of their context++ percentile scores (Agarwal, V., et al. Elife, 2015. 4) as these scores do not account for viral genome context. Targets appearing two or more times within a single transcript were counted only once per 3' UTR. Six targets from miRARE match the endogenous human 3'UTR for MECP2 (miR-9-5, miR-26b-5p, miR23a-3p, miR-218-5p, miR-27a-3p, and let-7-5p/98-5p). Five targets from miRARE match the endogenous mouse 3'UTR for MECP2 (miR-26b-5p, miR-23a-3p, miR-218-5p, miR-27a-3p, and let-7-5p/98-5p).

Weekly Weighing and Aggregate Behavior Scoring: An aggregate phenotype severity scale was used to assess behavior in treated mice and is based on a previously published scale (Guy, J., et al. Science, 2007. 315(5815): p. 1143-7). This aggregate scale includes 6 sub-scales for abnormal mobility, abnormal gait, hindlimb clasping, tremors, abnormal breathing, and abnormal general appearance. Hindlimb clasping was assessed by lifting the mouse by the tail so that hindlimbs were suspended. Scorers were blind to treatment and genotype, but may be able to infer genotype through visual assessment. Mice were weighed and scored pre-injection and weekly thereafter.

Rotarod: Mice were tested on a Columbus Instruments Rotamex-5. The rotarod accelerated from 4-40 rpm over 5 min. Mice were tested in 4 trials per day over 2 days with 15-min intervals between trials. The recorded latency was either the time at which the mouse fell from the rotarod or the time at which the mouse spun once around the rod without falling (the mouse would then be removed from the rotarod). These assessments were done with scorers blind to treatment and genotype.

Survival: The date of death recorded for each mouse was the natural date of death with the following exceptions: Mice that lost at least 20% of their peak body weight were euthanized, according to previously published methods (Gadalla, K. K. E., et al. Mol Ther Methods Clin Dev, 2017. 5: p. 180-190), or upon the recommendation of UT Southwestern Animal Resource Center veterinary staff. Early euthanasias for severe health problems (prolapse with complications, tail lesions resulting in necrosis or followed by self-injury) are indicated in the uncensored survival curves.

Immunofluorescence and Confocal Analyses: Immunofluorescence analyses art were conducted according to previously published methods (Sinnett, S. E., et al. Mol Ther Methods Clin Dev, 2017. 5: p. 106-115) with the following exception: antigen retrieval was not performed. Antigen retrieval is necessary prior to blocking and incubating with anti-MeCP2 primary antibodies, but not prior to blocking and incubating with anti-myc antibody. Immunolabeled sections were imaged with a Zeiss 880 confocal microscope using Zen software at UT Southwestern's Live Cell Imaging Facility.

Statistical Analyses: The alpha-level used to determine significance was $p<0.05$. Statistical analyses of transformed signal intensities from miRNA microarray was performed according to methods described in their technical bulletin. Analyses between groups were performed (e.g., group A vs. B). Due to limitations of the screening technique, p-values were interpreted with caution, and both screening and bioinformatics results were merged to justify miRNA targets selected for miRARE. The Gehan-Breslow-Wilcoxon test was used to calculate statistical significance between pairs of groups in Kaplan-Meier plots generated by GraphPad Prism. Except where otherwise noted, GraphPad was used to conduct two-way ANOVAs followed by Tukey's post-hoc test for weight and behavior data.

Example 1—MiniMECP2 Vectors can Cause Side Effects in WT Mice

Figure 1C:
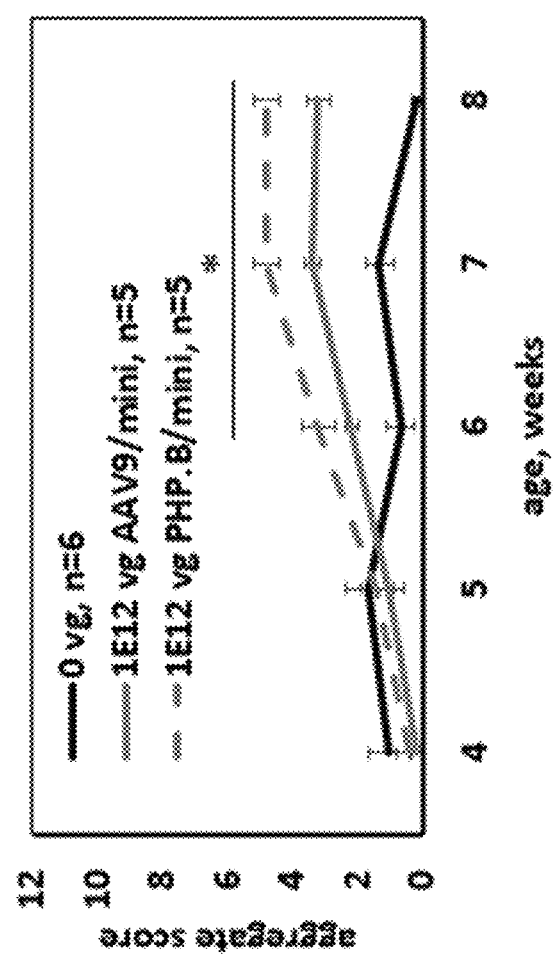

AAV9/MeP426-hMF(P2-myc-RDH1pA (hereafter referred to as AAV9/MECP2) can cause dose-dependent side effects (e.g., weight loss and limb clasping abnormalities) after intracisternal (ICM) administration in adolescent mice. In contrast, relatively little is known regarding the safety of AAV9/miniMECP2. To assess toxicity from miniMECP2 gene transfer, WT adolescent mice were injected with $1\times10^{12}$ vg of AAV9/or PHP.B/miniMECP2 (ICM) and scored behavior weekly. While these doses are extremely high, the goal is to develop a treatment that permits widespread MeCP2 protein expression in the CNS—and may therefore require a high dose—without causing side effects. AAV9/miniMECP2 increased mean clasping scores within two weeks after injection ($p<0.05$; FIG. 1A). PHP.B/miniMECP2 resulted in bilateral clasping as early as 3 days after injection (FIG. 1B). Both AAV9/and PHP.B/miniMECP2 increased aggregate phenotype severity scores within 2 weeks after injection ($p<0.05$; FIG. 1C). Although transgenic mice expressing endogenous miniMeCP2-EGFP exhibit mild clasping, the observed rapidly developing severe phenotypes is consistent with toxic overexpression and therefore warranted further optimization of the miniMECP2 viral genome.

Example 2—MicroRNA (miRNA) Expression Analysis to Design miRARE Sequence

To identify miRNAs upregulated by toxic MECP2 gene therapy, WT and KO mice were injected with saline, AAV9/EGFP, or AAV9/MECP2 at 4-5 weeks of age ($1\times10^{12}$ vg/mouse, ICM). Two to three weeks after injection, three types of tissue found close to the injection site were dissected. The tissue types were cervical cord (CC), cerebellum, and medulla. Total RNA was purified from these samples. Then, the expression of 1900 mouse miRNAs were quantified via microarray. This approach enabled identification of MeCP2-responsive miRNAs that are relevant within the CNS while forgoing the possibility of more granular, cell-type specific miRNA identification. The miRNAs whose expression levels were significantly increased at the tissue level in correlation with MeCP2 were identified. Given that these changes were too small in scale (most are <1.5 fold) for secondary confirmation with qRT-PCR, an alternative secondary approach to justify the selection of miRNA targets for a new regulatory panel was used.

Figure 2A:
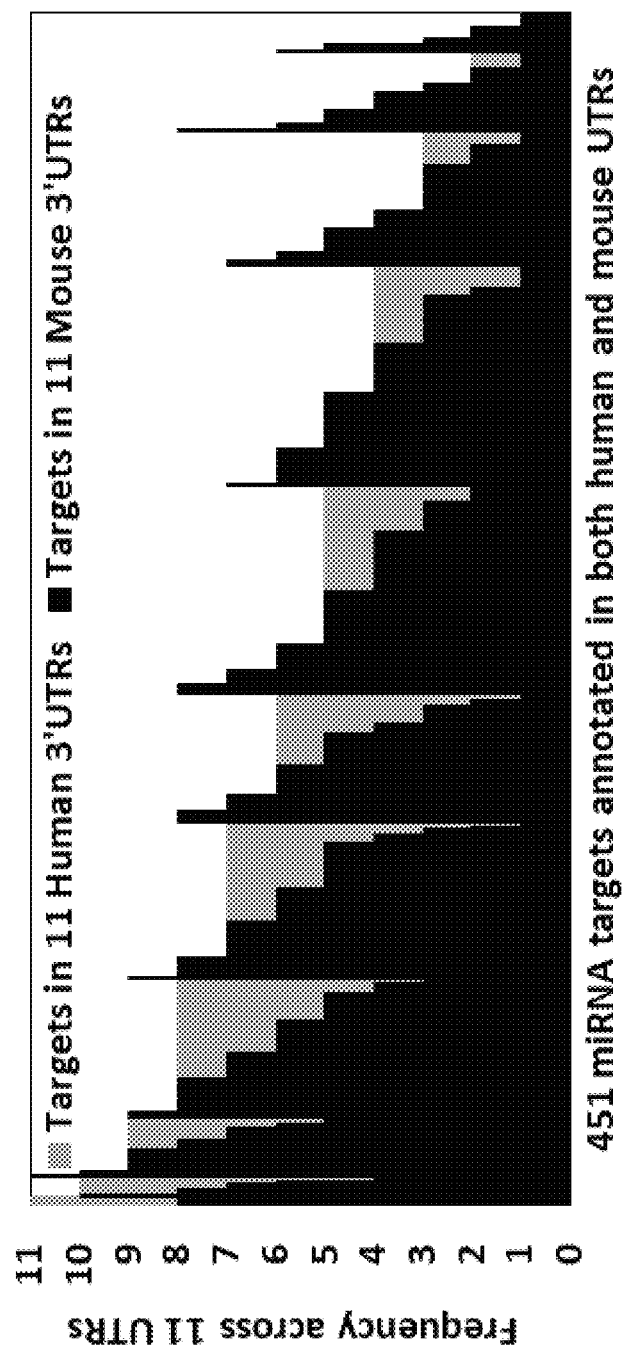
FIG. 2A-C shows microarray expression data used to rank targets that appear frequently across a curated list of 3' UTRs for genes mediating intellectual disability.
Figure 2B:
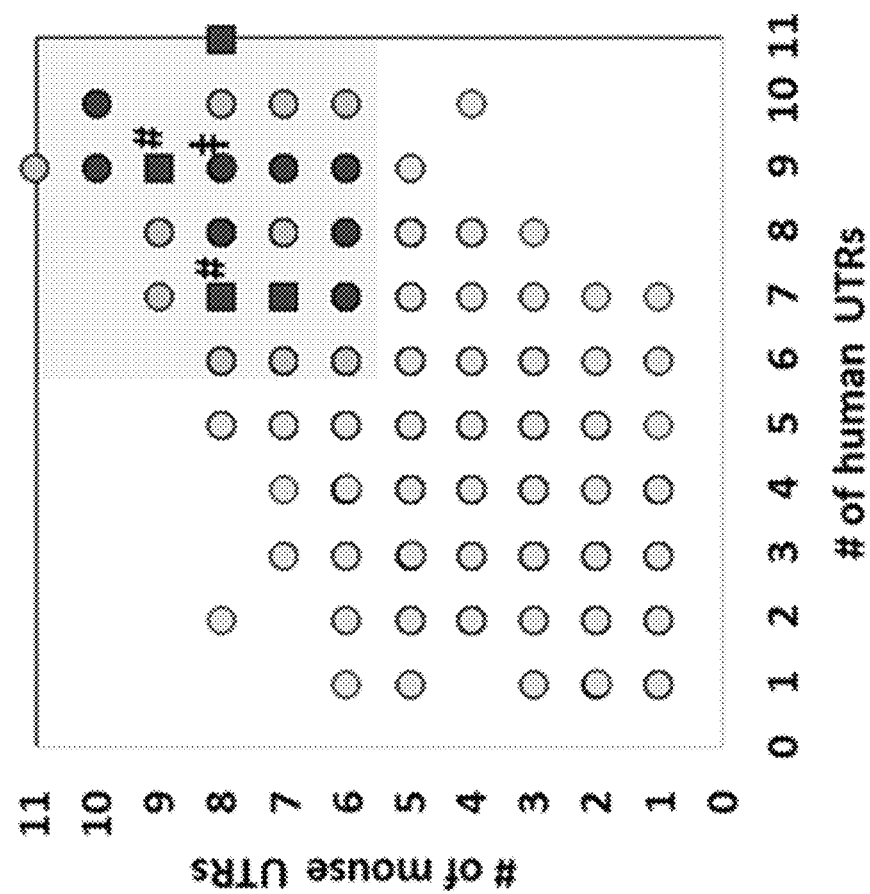
Figure 5:
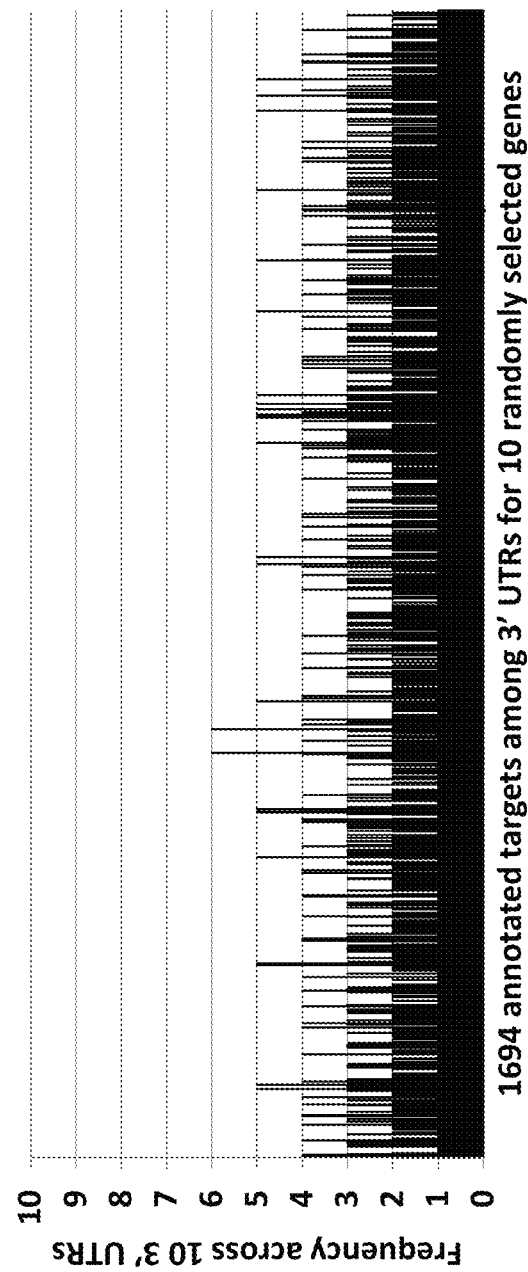
FIG. 5 is a graph depicting ten randomly selected human 3' UTRs have few miRNA targets in common. 3' UTRs were examined for ACTB, beta-actin; ATF1, activating transcription factor 1; DAD1, defender against cell death 1: DARS, aspartyl-tRNA synthetase; GAPDH, glyceraldehyde-3-phosphate dehydrogenase; HSPA4, heat shock protein family A (Hsp70) member 4; MRPL9, mitochondrial ribosomal protein L9; POLR1C, RNA polymerase I and III subunit C; PRKAG1, protein kinase AMP-activated non-catalytic subunit gamma 1; RPL5, ribosomal protein L5.
Figure 7B:
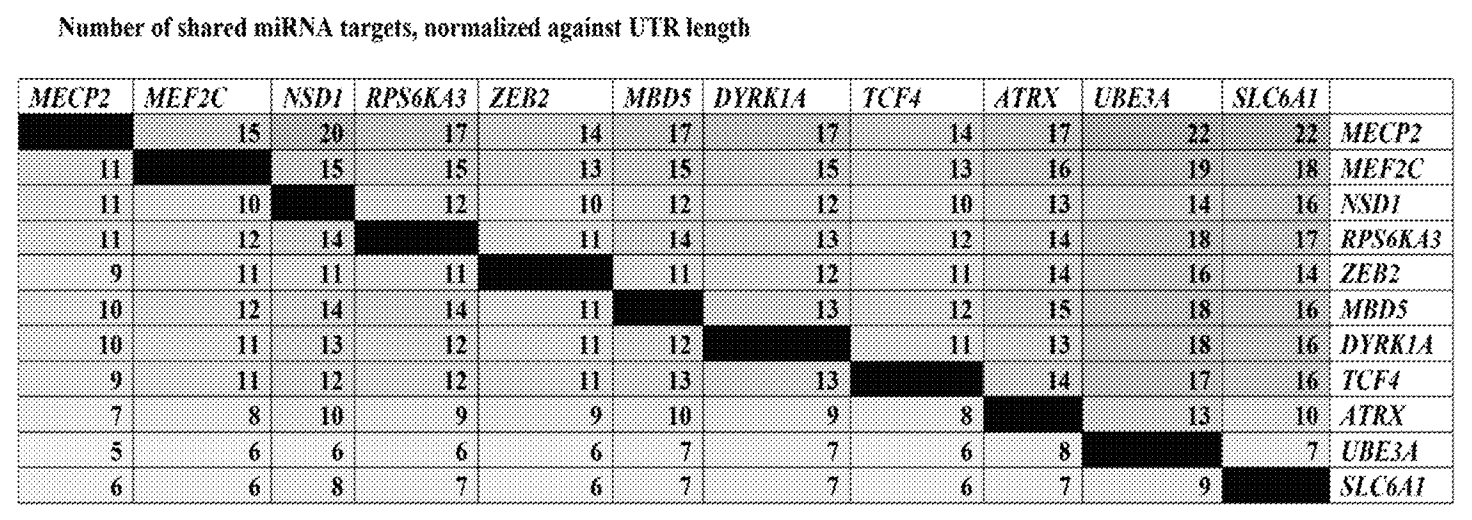

Given the need for a secondary approach, microarray data was merged with a new bioinformatics approach. The 3' UTRs of dose-sensitive CNS genes mediating phenotypically-related and developmentally-concurrent neurodevelopmental disorders may have a number of miRNA targets in common (Tables 2-3). If so, a compact, multi-purpose target panel that is primarily intended for Rett gene therapy but can also be relevant for other diseases can be designed. The number of times annotated miRNA targets appeared among eleven 3' UTRs was quantified for a curated list of genes mediating intellectual disability (Tables 2-3; FIG. 2A-B). To address the concern that apparent conservation of targets across our curated list of 3' UTRs may be an artifact of extremely long mRNA sequences, the same analysis was conducted for a random selection of human genes. It was observed that: (1) The 3' UTRs for randomly selected genes had few miRNA targets in common (FIG. 5); and (2) The number of shared targets per 100 bp length of 3' UTR sequence was lower for the randomly selected gene set than for our curated gene set (FIGS. 6A-B and 7A-B).

TABLE 2

Curated list of confirmed or putative dose-sensitive genes mediating intellectual disability.

| Gene | Role | Loss-of function syndrome | Monogenic mouse model | Clinical polygenic syndrome | Human ensemble transcript #[a] |
|---|---|---|---|---|---|
| MECP2 | Transcription | RTT | ✓ | ✓ | ENST00000303391.6 |
| TCF4 | Transcription | Pitt-Hopkins | ✓ | ✓ | ENST00000354452.3 |
| MEF2C | Transcription | MEF2C Haplo-insufficiency | — | ✓ | ENST00000340208.5 |
| NSD1 | Transcription | Sotos | — | ✓ | ENST00000439151.2 |
| ATRX | Transcription | ATRX | ✓ | ✓ | ENST00000373344.5 |
| MBD5 | Transcription | MAND | — | ✓ | ENST00000407073.1 |
| ZEB2 | Transcription | Mowat-Wilson | — | ✓ | ENST00000558170.2 |
| UBE3A | Degradation and Transcription | Angelman | ✓ | ✓ | ENST00000232165.3 |
| DYRK1A | Phosphorylation | DYRK1A | ✓ | ✓ | ENST00000339659.4 |
| RPS6KA3 | Phosphorylation | Coffin-Lowry | — | ✓ | ENST00000379565.3 |
| SLC6A1 | Transporter | Doose | ✓ | ✓ | ENST00000287766.4 |

Inactivating mutations in the genes listed in Table 2 have been shown to mediate neurodevelopmental disorders characterized by intellectual disability as well as other phenotypes, such as seizures, stereotypies, abnormal speech, and/or abnormal head size. Although the exact age of onset varies across loss-of-function syndromes, many of these syndromes are evident by 2 years of age. Reciprocal (overexpression-related) disorders may be mediated wholly or in part by the same genes. The contribution of a specific gene to specific phenotypes associated with a human chromosomal duplication may not always be known. To be clear, patients with supernumerary protein expression typically have duplications spanning larger chromosomal regions that encompass—but are not limited to—the genes indicated in this table. Therefore, Table 3 includes monogenic duplication mouse models that underscore the potential dose-sensitivity of these genes. Clinical vignettes describing intragenic duplications (which may yield truncated protein) are not considered in this table. 3' UTR sequences are accessible at targetscan.org. The ensemble transcript numbers listed here were used for analyses (Agarwal, V., et al. Elife, 2015. 4).

Figure 2C:
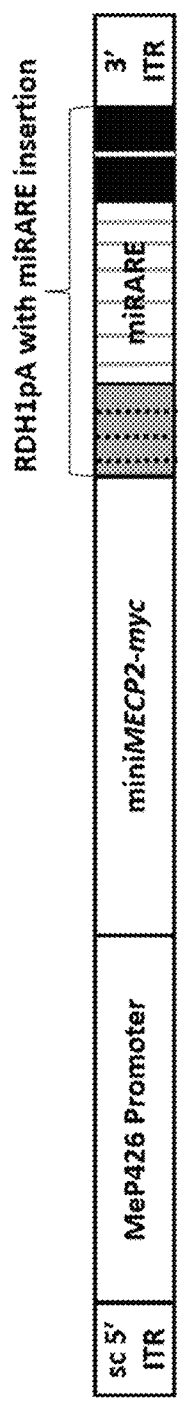

After identifying miRNA targets that appear across most (≥6) of the 11 3' UTRs (in both mouse and human data sets), microarray data was used to prioritize targets for miRNAs expressed in tissue near the intraCSF injection site (FIGS. 2A-B). The list of the candidate targets was then narrowed to include those for miRNAs whose expression levels appeared to increase in correlation with MeCP2. Finally, regulatory potential while minimizing DNA sequence length was maximized by including a let-7-5p binding site predicted to base pair with multiple potentially MeCP2-responsive let-7-5p miRNAs. Ultimately, this two-pronged approach yielded a 175 bp 6-target panel (miRARE) which was inserted into the miniMECP2 viral genome (FIG. 2C). The self-complementary AAV9/MeP426-miniMECP2-myc-miRARE-RDH1 pA viral genome is hereafter referred to as AAV9/miniMECP2-miRARE. Importantly, each of these miRARE targets are predicted to bind miRNAs that have been shown to be expressed in human brain tissue, from infancy through adolescence. Furthermore, the relative expression levels of 6 female human cerebellar miRNAs (miR-9-5p, miR-26b-5p, miR-23a-3p, miR-218-5p, miR-27a-3p, and let-7e-5p) roughly mirrors the relative expres-

TABLE 3

Phenotypic overlap among selected loss-of-function disorders and reciprocal duplication disorders that encompass the same genes.

| | Loss-of-function phenotypes | | | | | Phenotypes in mono- or polygenic duplication disorders[a] | | | | |
|---|---|---|---|---|---|---|---|---|---|---|
| Gene | Stereotypy | Microcephaly | Seizures | Speech abnormalities | Intellectual disability | Intellectual disability | Speech abnormalities | Seizures | Microcephaly | Stereotypy |
| TCF4 | ✓ | ✓ | ✓ | ✓ | ✓ | ✓ | | ✓ | ✓ | |
| MECP2 | ✓ | ✓ | ✓ | ✓ | ✓ | ✓ | ✓ | ✓ | ✓ | ✓ |
| UBE3A | ✓ | ✓ | ✓ | ✓ | ✓ | ✓ | ✓ | ✓ | ✓ | |
| DYRK1A | ✓ | ✓ | ✓ | ✓ | ✓ | ✓ | ✓ | ✓ | ✓ | ✓ |
| MEF2C | ✓ | | ✓ | ✓ | ✓ | ✓ | ✓ | | ✓ | |
| NSD1 | | | ✓ | ✓ | ✓ | ✓ | ✓ | ✓ | ✓ | |
| ATRX | ✓ | ✓ | ✓ | ✓ | ✓ | ✓ | ✓ | ✓ | | |
| RPS6KA3 | | ✓ | ✓ | ✓ | ✓ | ✓ | ✓ | ✓ | | |
| MBD5 | ✓ | | ✓ | ✓ | ✓ | ✓ | ✓ | ✓ | ✓ | |
| ZEB2 | | ✓ | ✓ | ✓ | ✓ | ✓ | ✓ | | ✓* | |
| SLC6A1 | ✓ | ✓ | ✓ | ✓ | ✓ | ✓ | ✓ | | ✓ | |

[a]Includes mouse monogenic duplication models, human polygenic duplications, and human trisomies. Mouse and human phenotypes are aggregated together in Table 2. Speech abnormalities may encompass multiple phenotypes, such as lack of speech, babbling, dysprosody, or delayed speech. The number and severity of symptoms may vary among patients with the same diagnosis. Early lethality in humans with duplication disorders may preclude documentation of specific phenotypes.
*Patient with 2q22.3 triplication had microcephaly at birth, but not at later age (Yuan. H., et al. Mol Cytogenet, 2015, 8: p. 99).

sion levels in the miRNA profile, with miR-9-5p and miR-23a-3p being expressed at high and low levels, respectively.

Example 3—MiRARE Improves Safety of miniMECP2 Gene Transfer in Treated WT Mice

The safety of regulated miniMECP2 gene transfer in two treatment paradigms for adolescent mice: (1) ICM PHP.B-mediated gene transfer (see FIG. 8); and (2) intrathecal (IT) AAV9-mediated gene transfer was analyzed.

Figure 8A:
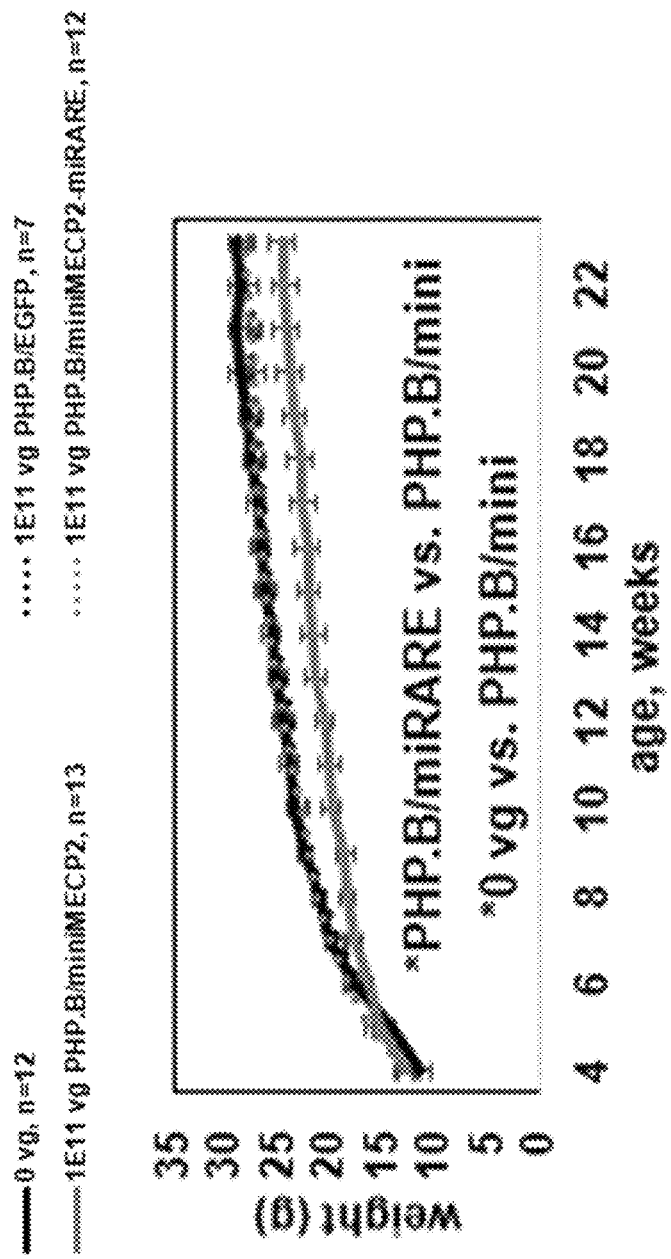
FIG. 8A-D shows miRARE protects against miniMECP2-mediated side effects in treated WT mice.
Figure 8B:
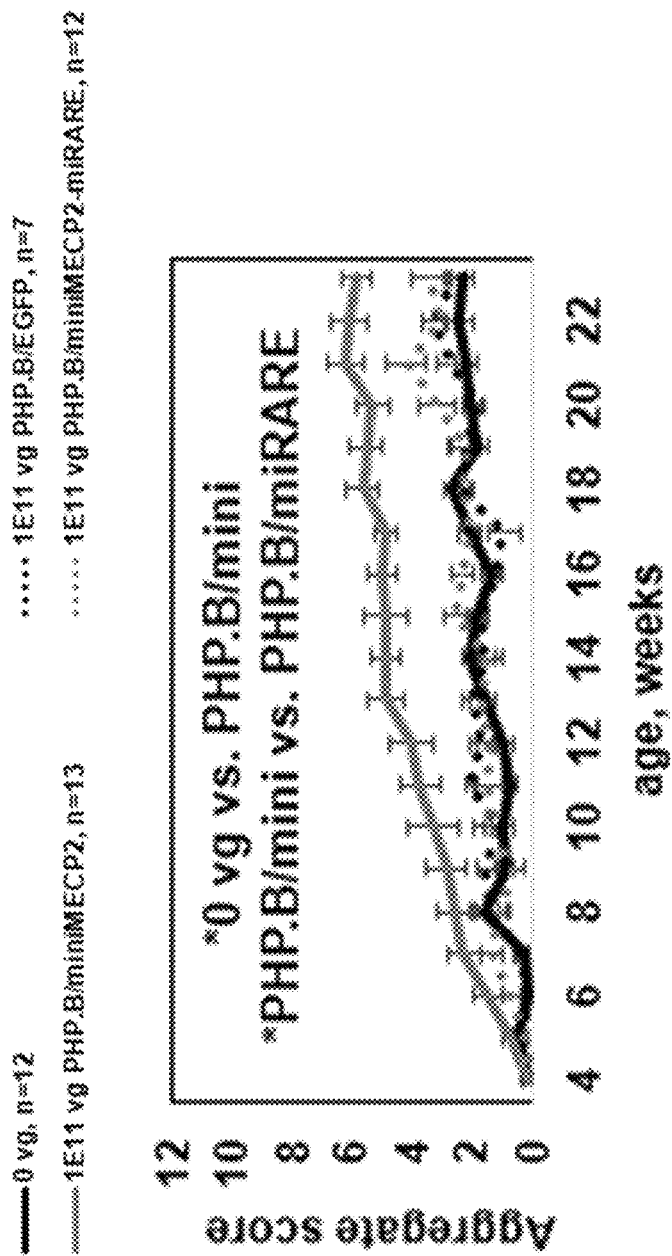
Figure 8C:
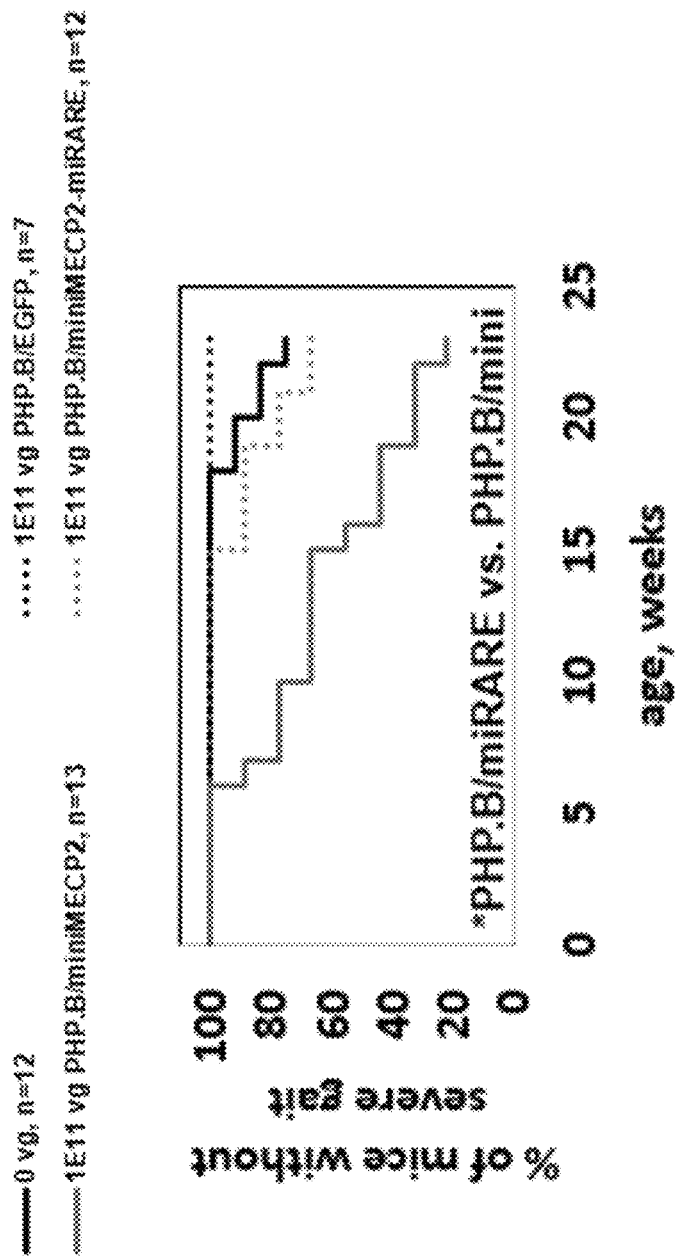
Figure 8D:
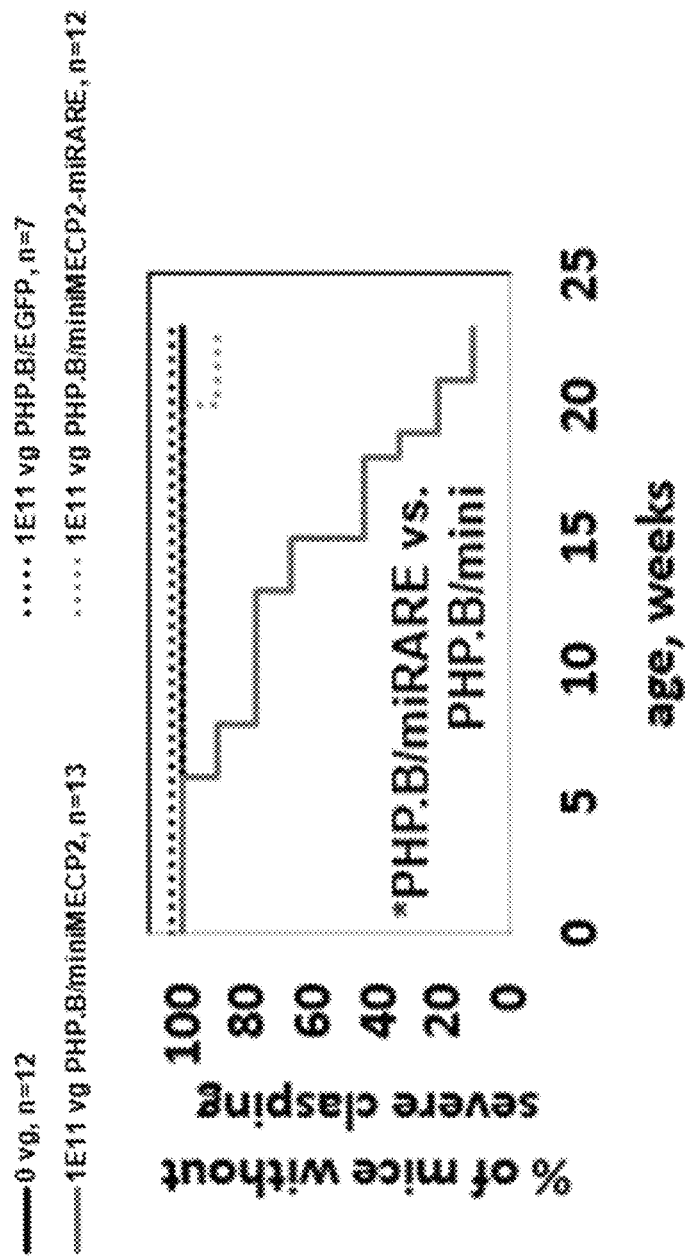

The ICM experiment with PHP.B provides data for highly efficient gene transfer and bridges the miRARE data with FIG. 1, which compares ICM administration of unregulated AAV9/and PHP.B/miniMECP2 vectors. The PHP.B data set is summarized: MIRARE provided robust regulation of miniMeCP2-myc protein expression in WT brains (miRARE decreases miniMeCP2-myc protein expression in the brain), prevented weight loss in virus-treated WT mice ($p<0.05$ vs. unregulated vector and vs. saline; FIG. 8A), normalized aggregate phenotype scores for virus-treated WT mice ($p<0.05$ vs. unregulated vector; FIG. 8B), delayed the onset of severe gait ($p<0.05$ vs. unregulated vector; FIG. 8C) and almost completely eliminated the occurrence of severe hindlimb clasping in virus-treated WT mice ($p<0.05$ vs. unregulated vector; FIG. 8D).

Figure 3A:
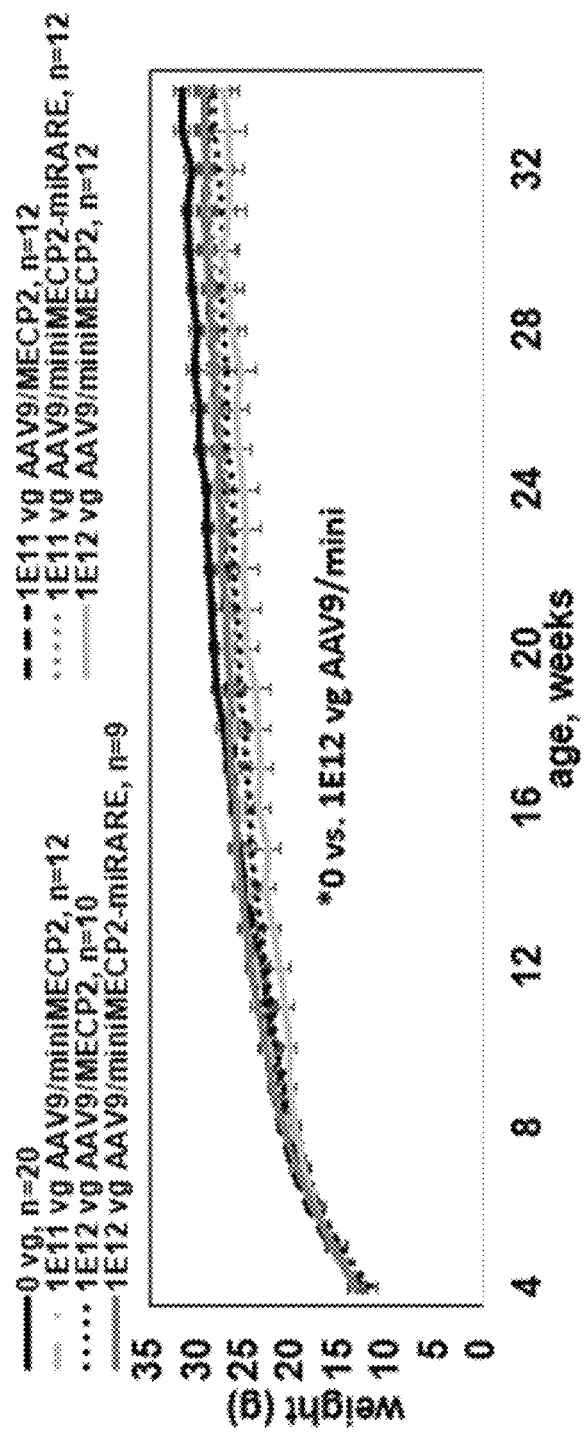
FIG. 3A-E shows AAV9/miniMECP2-miRARE is well-tolerated after IT administration in WT adolescents. Throughout this manuscript, all treatments were administered between 4-5 weeks of age.

Next, to align the miRARE assessment with methods relevant for human translation, miRARE within the context of intrathecally administered AAV9 was evaluated. MiRARE provided several safety benefits. Specifically, miRARE prevented acute miniMECP2-mediated weight loss in WT mice at the highest dose tested ($1\times10^{12}$ vg/mouse; FIG. 3A). AAV9/miniMECP2-treated WT mice had significantly lower weight than that of saline-treated WT mice beginning at 15 weeks of age ($p<0.05$). No significant difference was observed between saline- and AAV9/miniMECP2-miRARE-treated WT mice ($1\times10^{12}$ vg/mouse).

Figure 3B:
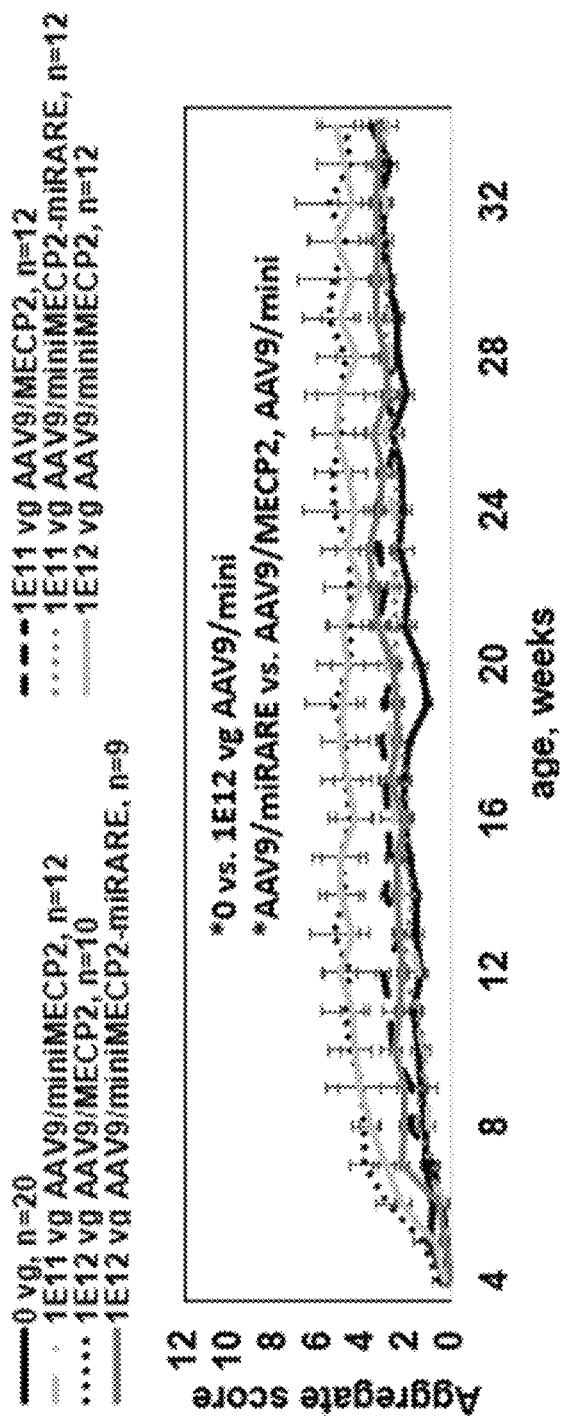
Figure 3C:
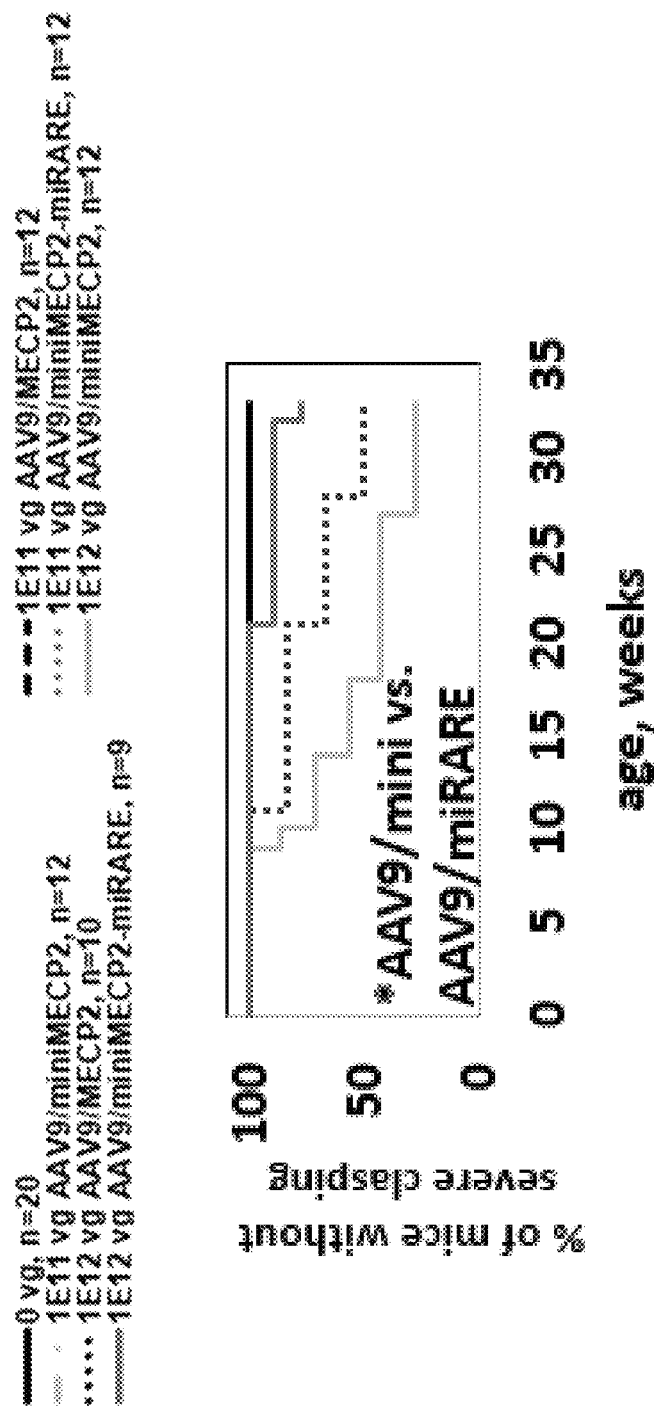
Figure 3D:
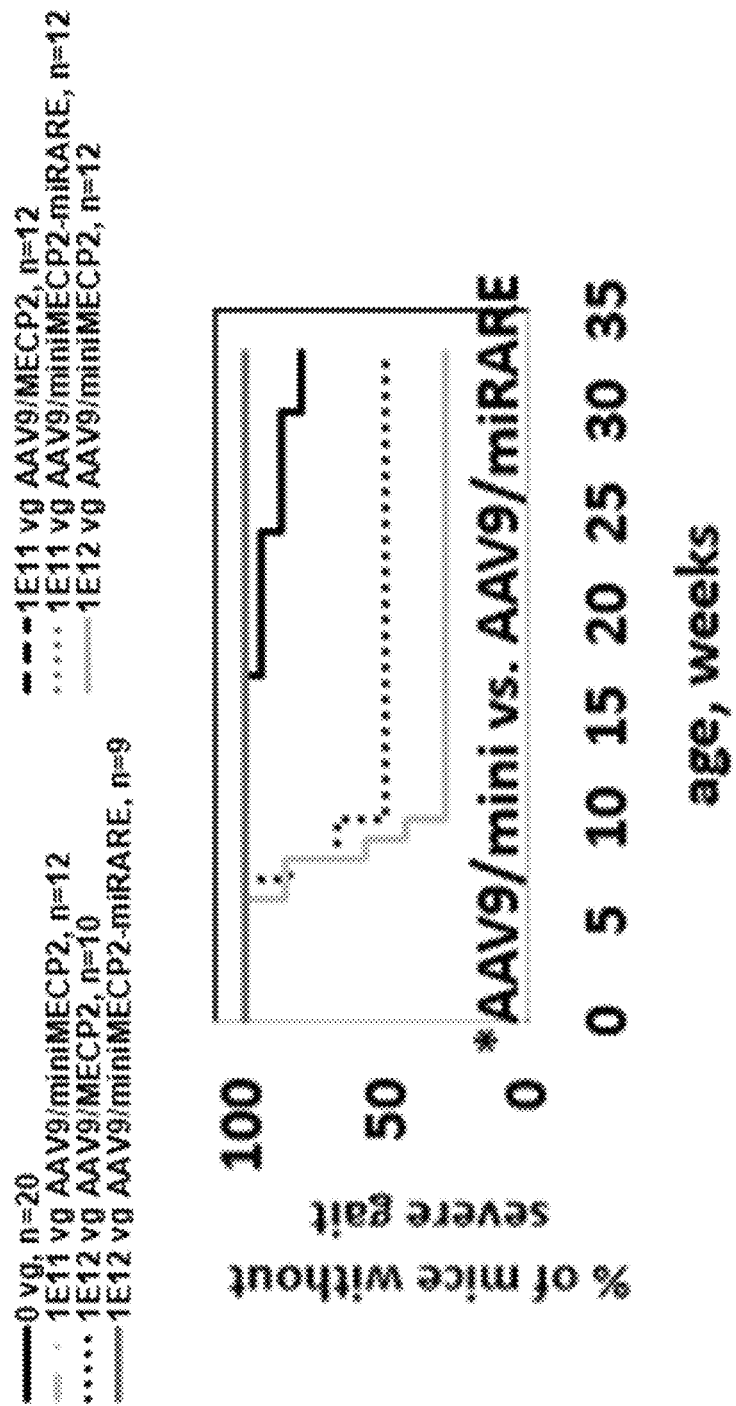

MiRARE attenuated miniMECP2-mediated aggravation in WT aggregate phenotype severity scores (FIG. 3B). AAV9/MECP2- and AAV9/miniMECP2-treated WT mice had a significantly higher mean aggregate behavioral severity score versus that observed for saline-treated mice ($p<0.05$; at 6-30 and 7-27 weeks of age, respectively). AAV9/miniMECP2-miRARE-treated WT mice had a significantly lower mean aggregate severity score versus those of AAV9/MECP2- and AAV9/miniMECP2-treated mice at most timepoints from 11-19 and 9-20 weeks of age, respectively. No significant difference was observed between saline- and AAV9/miniMECP2-miRARE-treated WT mice ($1\times10^{12}$ vg/mouse). The miRARE attenuated miniMeCP2-mediated aggravation in aggregate severity scores by reducing the frequency of miniMeCP2-mediated severe hindlimb clasping and by preventing miniMeCP2-mediated severely abnormal gait (FIGS. 3C-D). In contrast, at least half of the WT mice treated with AAV9/MECP2 or AAV9/miniMECP2 developed severely abnormal gait or severe hindlimb abnormalities.

Figure 3E:
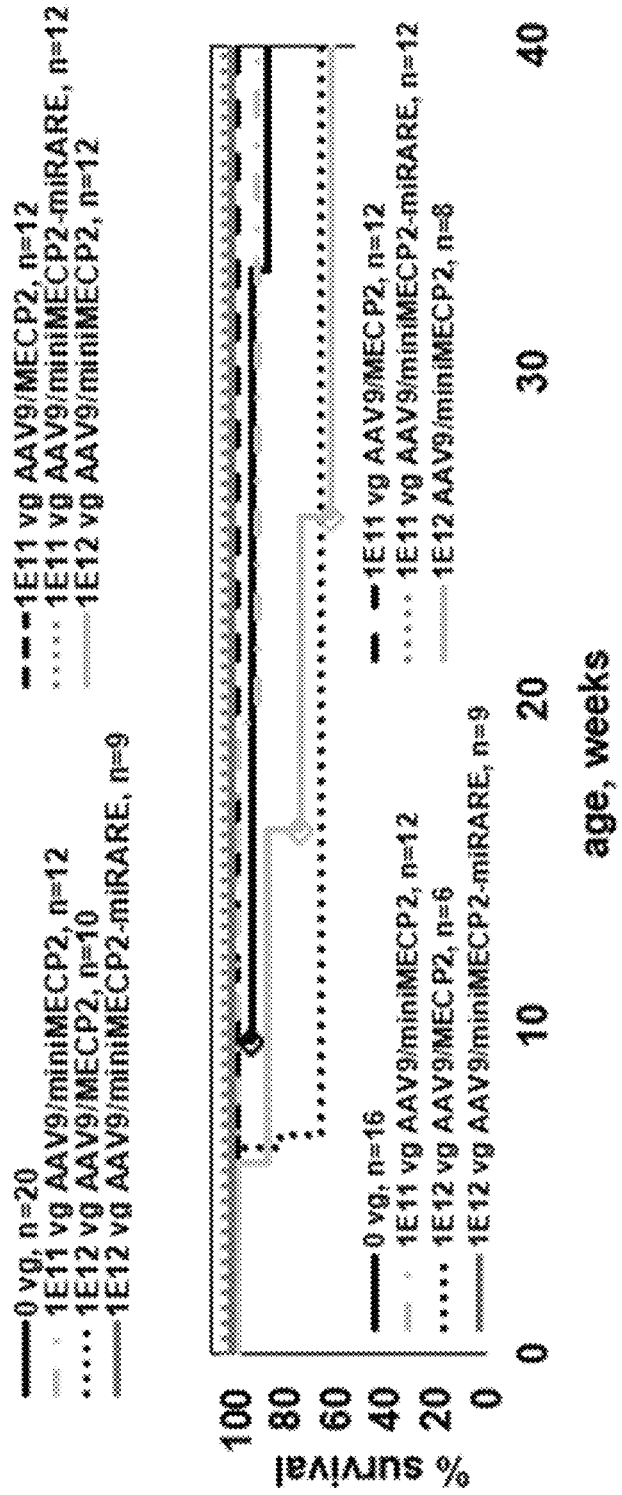

No early deaths were observed among AAV9/miniMECP2-miRARE-treated WT mice. Early veterinarian-requested euthanasias among AAV9/miniMECP2-treated WT mice were for complications from prolapses (FIG. 3E). Finally, no tail lesions were observed among AAV9/miniMECP2-miRARE-treated WT mice (0% of 21 mice). In contrast, lesions were observed in 8-17% of unregulated AAV9/miniMECP2-treated WT mice (1 of 12 mice treated with $1\times10^{11}$ vg; 2 of 12 mice treated with $1\times10^{12}$ vg). A tail lesion was observed in 1 of 12 WT mice treated with $1\times10^{11}$ vg AAV9/MECP2. These results demonstrate that the miRARE sequence can be used to effectively prevent adverse side-effects of AAV-mediated delivery of MECP2.

Example 4-AAV9/miniMECP2-miRARE Extends the Survival of MECP2 KO Mice

In the context of IT administration of AAV9 vectors in juvenile mice, unregulated miniMECP2 gene transfer failed to extend MECP2 KO survival at either dose tested. Regulated miniMECP2 gene transfer, however, extended KO survival by 56% ($1\times10^{12}$ vg/mouse; FIGS. 4A-E and FIG. 9). Although there is an apparent trend for increased survival of KO mice treated with AAV9/MECP2, this increase was not significant ($p=0.1$). Although there is a strong trend toward increased survival with AAV9/MECP2, studies in WT mice showed unacceptable toxicity with this vector design at this dose (FIGS. 3A-E). No treatment affected KO weight. These results demonstrate that the miRARE sequence can be used to effectively prevent adverse side-effects of AAV-mediated delivery of MECP2 while still providing therapeutic benefit and increasing survival of KO mice.

Example 5—AAV9/miniMECP2-miRARE Delays the Age of Onset of Severely Abnormal Gait Weekly behavior data was used to tabulate the approximate age of onset for severely abnormal gait in KO mice (score=2 on a scale of 0-2). AAV9/miniMECP2-miRARE delayed the approximate age of onset of severely abnormal gait by 4-5 weeks ($p<0.05$ versus all other groups; one-way ANOVA followed by Tukey's post hoc test), with a similar or lower frequency of occurrence (versus all other KO groups; FIGS. 4A-E).

In the accelerated rotarod test, AAV9/miniMECP2-miRARE ($1\times10^{12}$ vg/mouse) yields a trend in improved initial motor coordination of KO mice by 150% versus that of saline-treated mice ($p>0.05$), but did not improve motor learning across trials. Rotarod tests were performed on a separate cohort of mice located at a second animal facility.

Adverse events were noted in some AAV-treated KO mice.

Figure 4A:
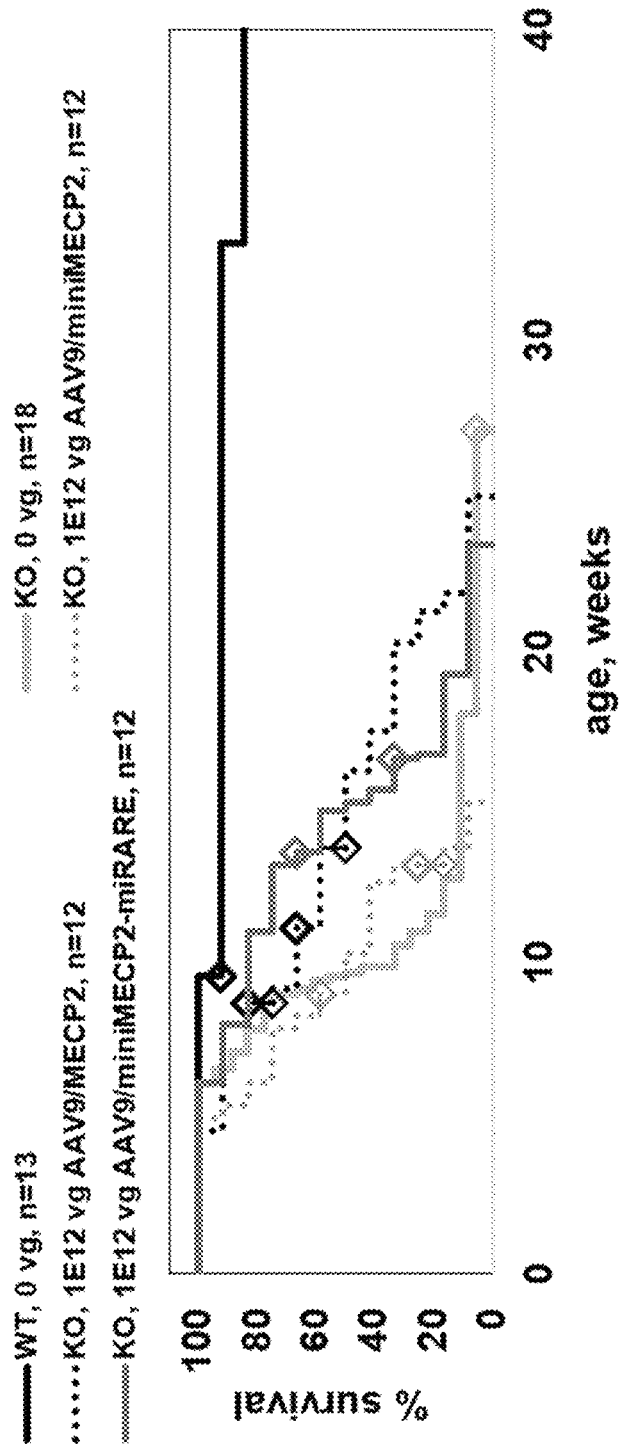
FIG. 4A-E shows AAV9/miniMECP2-miRARE extends the survival of KO mice.
Figure 4B:
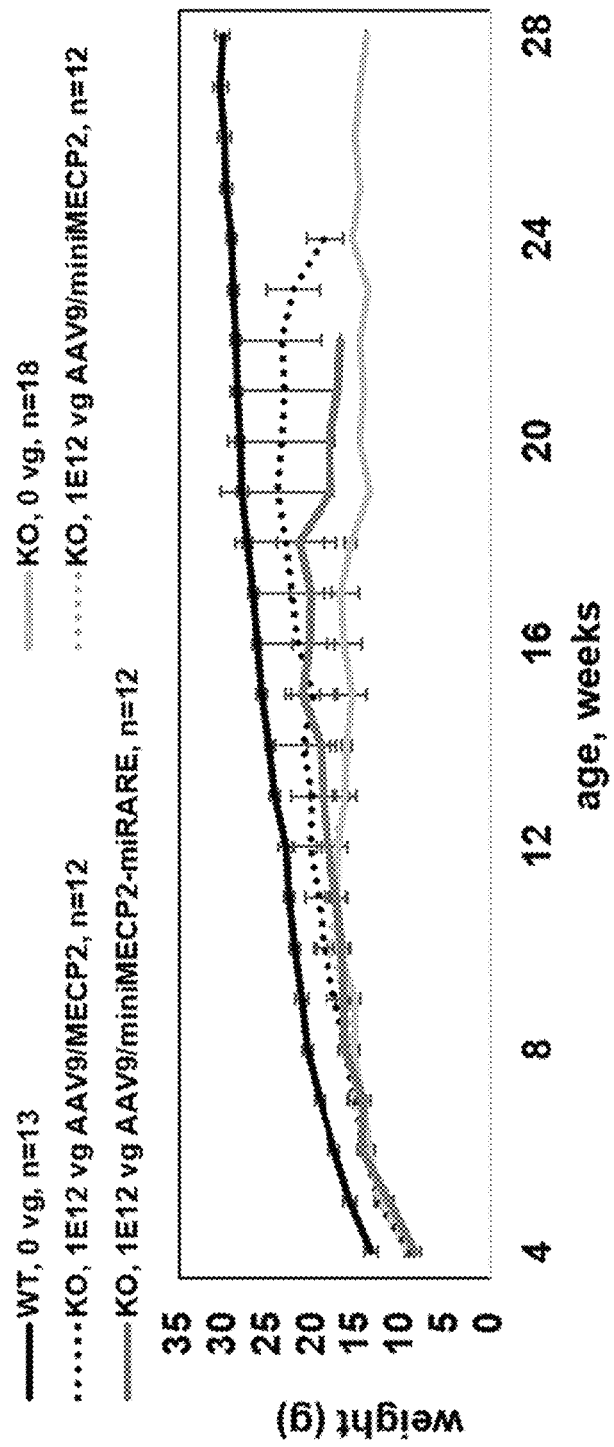
Figure 4C:
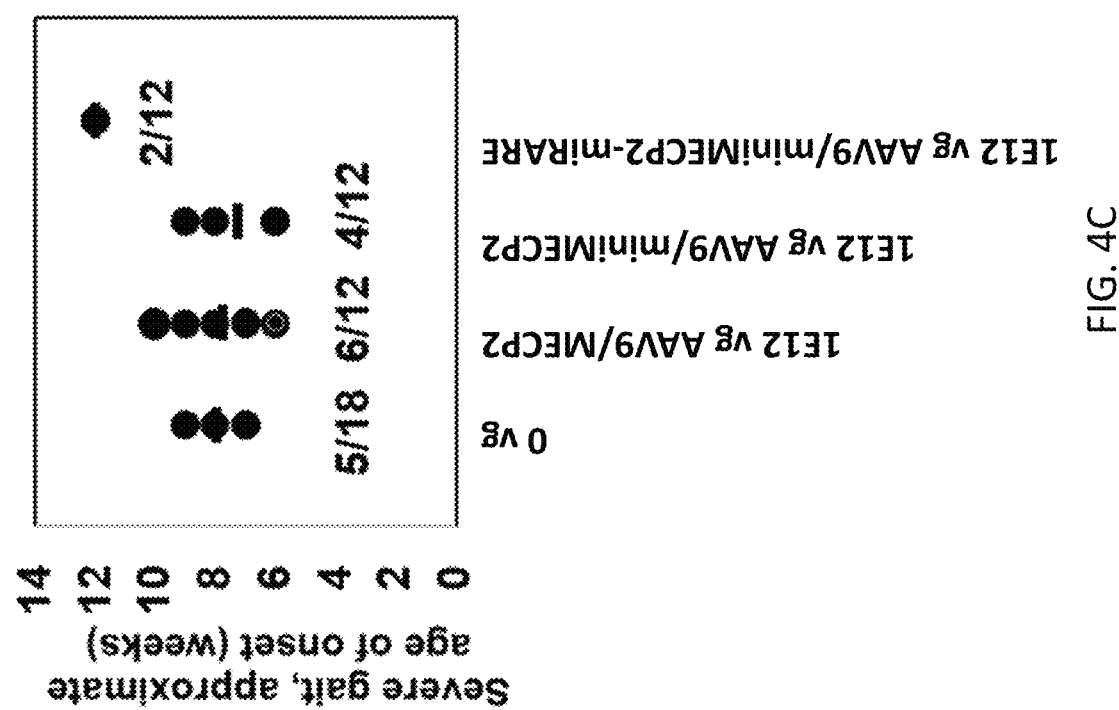
Figure 4D:
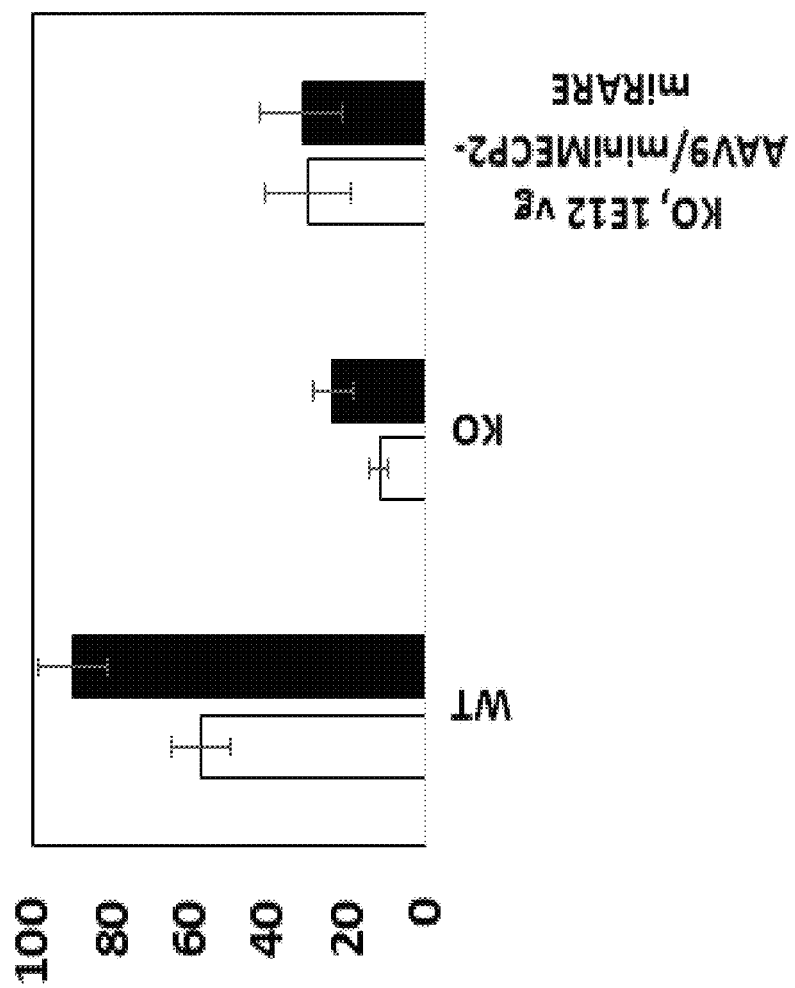
Figure 4E:
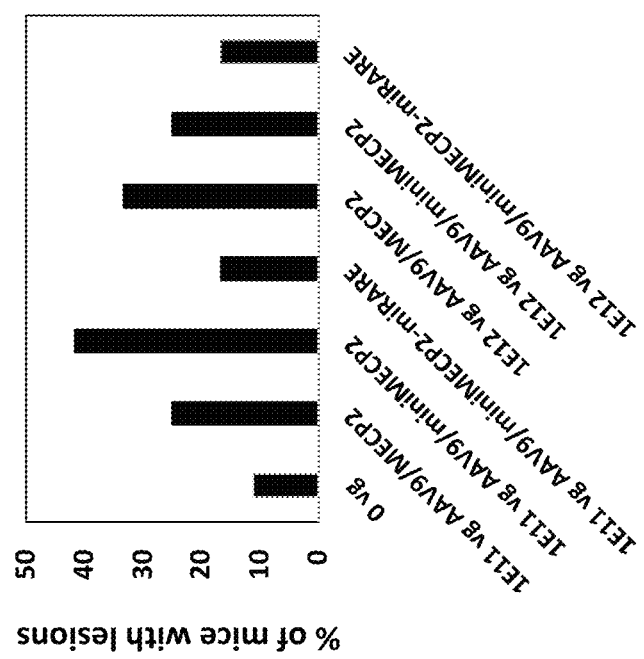
Figure 9:
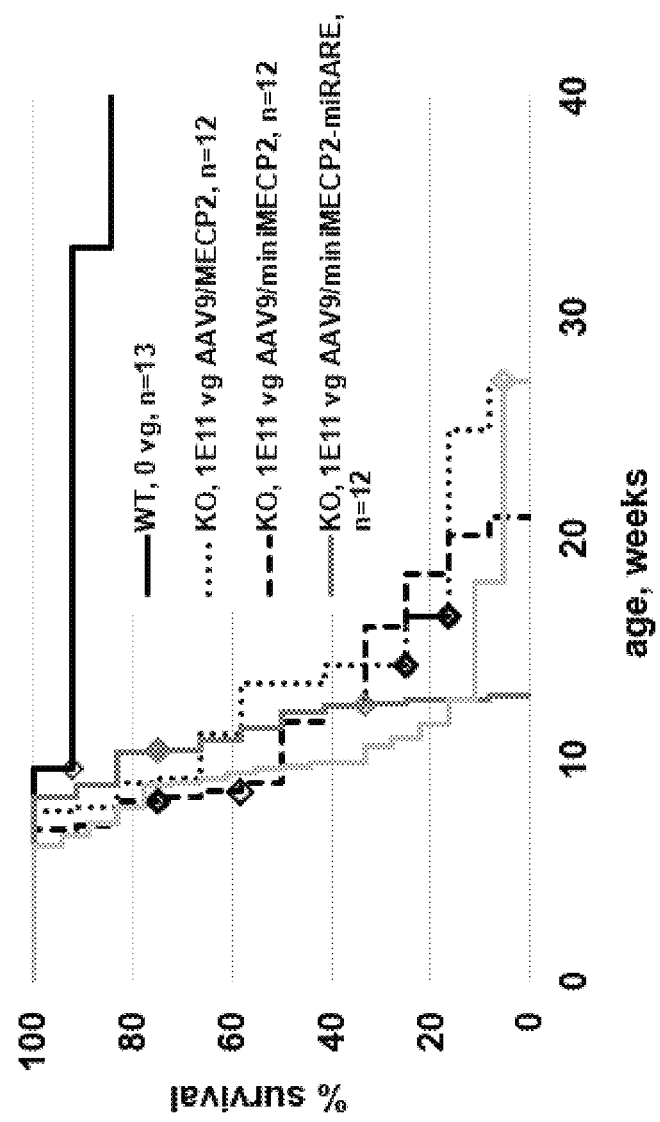
FIG. 9 is a graph depicting at $1 \times 10^{11}$ vg/mouse, none of the intrathecal treatments were effective at extending KO survival. Diamonds indicate veterinarian-requested euthanasias. The same saline-treated control groups appear in FIGS. 3-4.

Tail lesions were observed across all treatment groups, including saline-treated KO mice (FIG. 4E). The frequency of lesions among KO mice treated with saline was 11% (2/18). The frequency of lesions among mice treated with $1\times10^{11}$ vg of AAV9/MECP2, AAV9/miniMECP2, and AAV9/miniMECP2-miRARE were 25% (3/12), 42% (5/12), and 17% (2/12), respectively. The frequency of lesions among KO mice treated with $1\times10^{12}$ vg of AAV9/MECP2, AAV9/miniMECP2, and AAV9/miniMECP2-miRARE were 33% (4/12), 25% (3/12), and 17% (2/12), respectively. Due to the small group sizes, we cannot confidently determine if miRARE decreases the risk of lesions. The inverse relationship between frequency of lesions and dose for AAV9/miniMECP2-treated KO mice may be an artifact of small group size or perhaps early death. The respective median survivals for KO mice treated with $1\times10^{11}$ or $1\times10^{12}$ vg AAV9/miniMECP2 are 10.4 and 9.6 weeks, respectively (FIG. 4A and FIG. 9).

Summary of Examples 1-5

The results presented in Examples 1-5 are the first to quantify the dose-dependent side effects of unregulated AAV9/miniMECP2 in WT mice. These side effects recapitulate those previously observed for AAV9/MECP2 and therefore warranted further improvements to the viral genome.

A new target panel design strategy was created to design a regulated miniMECP2 viral genome featuring a "miRARE" miRNA target panel. Without wishing to be bound by theory, the goal was to utilize endogenous MeCP2-responsive miRNAs to downregulate the miniMECP2 transgene in the event of MeCP2 overexpression in order to create a safety valve to block transgene overexpression in any transduced cell. MiRARE meets the following criteria: (1) Most of the targets are predicted to bind putative MeCP2-responsive miRNAs; (2) Each target appears among 7-11 endogenous human 3' UTRs from a curated list of dose-sensitive genes mediating intellectual disability (and may therefore be useful for other dose-sensitive CNS gene therapy applications); and (3) The targets are predicted to bind miRNAs that are expressed in human CNS tissue across developmental stages. Ultimately, the strategy resulted in the design of a regulated viral genome that improved safety without compromising efficacy (versus that of the unregulated control vector) in two different treatment models.

The design strategy for miRARE seeks to address limitations of conventional approaches for regulating transgene expression within the context of CNS gene therapies. Previous approaches for regulating expression include strategies to impart cell-type specificity (e.g., neuronal promoters), eliminate peripheral expression (e.g., miR-122 target panels to constitutively inhibit hepatic expression), destabilize mRNA (in a manner that is not responsive to total MeCP2 levels) and destabilize exogenous protein (e.g., fused degron domains) (Luoni, M., et al. Elife, 2020. 9; Qiao, C., et al. Gene Ther, 2011. 18(4): p. 403-10; Geisler, A., et al. Gene Ther, 2011. 18(2): p. 199-209; Gray, S. J., et al. Hum Gene Ther, 2011. 22(9): p. 1143-53; Quintino, L., et al. Mol Ther Methods Clin Dev, 2018. 11: p. 29-39). These prior approaches, however, do not intend to cap exogenous protein expression levels in CNS cells receiving 100s of vector genome copies versus those of CNS cells receiving few genome copies. Moreover, conventional regulatory approaches are not intended to control expression in response to MeCP2 mosaicism, in which transduced cells express either WT endogenous MeCP2 or mutant MeCP2. This variability in vector copy number and endogenous WT MeCP2 expression across transduced cells creates a need for true feedback-enabled regulation of MeCP2. At the organismal level, such a feedback loop should maintain efficacy while improving safety. Ultimately, miRARE attenuates overexpression-related side effects in WT mice without compromising efficacy in KO mice.

miRARE improves both safety and efficacy of intrathecal miniMECP2 gene transfer (in WT and KO mice, respectively) without requiring a secondary intervention (FIGS. 4A-E). Because the miRARE vector was well-tolerated in WT mice, it is envisioned that the vector to be well-tolerated in allele-specific RTT models. Overall, miRARE greatly attenuated these WT behavioral side effects while improving KO survival in our lumbar intrathecal treatment model (FIGS. 4A-E).

The results presented in Examples 1-5 also demonstrate that MiRARE can have practical use beyond Rett syndrome. The miRARE sequence was designed using a combination of empirical data gathered from MeCP2 overexpression studies, but also integrated knowledge gained from the analysis of several developmentally-regulated, dose-sensitive genes. Thus, miRARE can be used to provide feedback regulation of other dose-sensitive genes in the context of gene transfer, including genes beyond those analyzed in the creation of miRARE. The design strategy of miRARE is of further significance because the target panel design strategy described herein is built upon molecular data from an intentional overdose. Risk-driven viral genome modification presents the field of gene therapy with a unique advantage that dose-dependent transgene-related side effects could be resolved within the encoded therapeutic product.

What is claimed is:

1. A method for treating Rett Syndrome in a subject in need thereof, comprising administering to the subject an rAAV viral vector, comprising (a) an AAV capsid protein and (b) an rAAV vector comprising, in 5' to 3' direction:
 (i) a first AAV ITR sequence comprising the nucleic acid sequence set forth in SEQ ID NO: 19;
 (ii) a promoter sequence comprising the nucleic acid sequence set forth in SEQ ID NO: 22;
 (iii) a transgene comprising the nucleic acid sequence set forth in SEQ ID NO: 3;
 (iv) a regulatory sequence comprising the nucleic acid sequence set forth in SEO ID NO: 13; and
 (v) a second AAV ITR sequence comprising the nucleic acid sequence set forth in SEQ ID NO: 21.

2. The method of claim 1, wherein the rAAV vector comprises the nucleic sequence set forth in SEQ ID NO: 29.

3. The method of claim 1, wherein the AAV capsid protein is an AAV9 capsid protein.

4. The method of claim 1, wherein the rAAV viral vector is administered intrathecally.

5. The method of claim 1, wherein at least about $10^{14}$ viral particles are administered.

6. The method of claim 1, wherein at least about $10^{15}$ viral particles are administered.

7. The method of claim 1, where in $10\times10^{14}$ viral particles are administered.

8. The method of claim 1, wherein about $10^{14}$ to about $10^{15}$ viral particles are administered.

9. The method of claim 1, wherein about $10^{14}$ to about $10^{15}$ viral particles are administered intrathecally.

10. The method of claim 1, wherein the regulatory sequence further comprises an RDH1polyA element comprising the nucleic acid sequence set forth in SEQ ID NO: 14.

11. The method of claim 1, wherein the regulatory sequence further comprises a MeCP2 downstream polyA element comprising the nucleic acid sequence set forth in SEQ ID NO: 16.

12. The method of claim 1, wherein the regulatory sequence comprises the nucleic acid sequence set forth in SEQ ID NO: 17.

13. An rAAV vector, comprising, in 5' to 3' direction
(i) a first AAV ITR sequence comprising the nucleic acid sequence set forth in SEQ ID NO: 19;
(ii) a promoter sequence comprising the nucleic acid sequence set forth in SEQ ID NO: 22;
(iii) a transgene encoding a MECP2 polypeptide, the transgene comprising the nucleic acid sequence set forth in SEQ ID NO: 3;
(iv) a regulatory sequence comprising the nucleic acid sequence set forth in SEO ID NO: 13; and
(v) a second AAV ITR sequence comprising the nucleic acid sequence set forth in SEQ ID NO: 21.

14. The rAAV vector of claim 13, wherein the regulatory sequence further comprises an RDH1 polyA element comprising the nucleic acid sequence set forth in SEQ ID NO: 14.

15. The rAAV vector of claim 13 wherein the regulatory sequence further comprises a MeCP2 downstream polyA element comprising the nucleic acid sequence set forth in SEQ ID NO: 16.

16. The rAAV vector of claim 13, wherein the regulatory sequence comprises the nucleic acid sequence set forth in SEQ ID NO: 17.

17. The rAAV vector of claim 13, wherein the rAAV vector comprises the nucleic sequence set forth in SEQ ID NO: 29.

18. An rAAV viral vector comprising the rAAV vector of claim 13 and an AAV capsid protein.

19. The rAAV viral vector of claim 18, wherein the AAV capsid protein is an AAV9 capsid protein.

20. A pharmaceutical composition comprising the rAAV viral vector of claim 19.

* * * * *

SEQUENCE LISTING

```
Sequence total quantity: 30
SEQ ID NO: 1           moltype = AA  length = 181
FEATURE                Location/Qualifiers
REGION                 1..181
                       note = miniMeCP2
source                 1..181
                       mol_type = protein
                       organism = synthetic construct
SEQUENCE: 1
MAAAAAAAPS GGGGGGEEER LEEKPAVPEA SASPKQRRSI IRDRGPMYDD PTLPEGWTRK   60
LKQRKSGRSA GKYDVYLINP QGKAFRSKVE LIAYFEKVGD TSLDPNDFDF TVTGRGSPSR  120
REQKPPGSSG SSGPKKKRKV PGSVVAAAAA EAKKKAVKES SIRSVQETVL PIKKRKTRET  180
V                                                                 181

SEQ ID NO: 2           moltype = AA  length = 180
FEATURE                Location/Qualifiers
REGION                 1..180
                       note = miniMeCP2
source                 1..180
                       mol_type = protein
                       organism = synthetic construct
SEQUENCE: 2
AAAAAAAPSG GGGGGEEERL EEKPAVPEAS ASPKQRRSII RDRGPMYDDP TLPEGWTRKL   60
KQRKSGRSAG KYDVYLINPQ GKAFRSKVEL IAYFEKVGDT SLDPNDFDFT VTGRGSPSRR  120
EQKPPGSSGS SGPKKKRKVP GSVVAAAAAE AKKKAVKESS IRSVQETVLP IKKRKTRETV  180

SEQ ID NO: 3           moltype = DNA  length = 543
FEATURE                Location/Qualifiers
misc_feature           1..543
                       note = miniMeCP2
```

```
source                  1..543
                        mol_type = other DNA
                        organism = synthetic construct
SEQUENCE: 3
atggccgccg ccgccgccgc cgcgccgagc ggaggaggag gaggaggcga ggaggagaga    60
ctggaagaaa agccggctgt gccggaagct tctgcctccc ccaaacagcg gcgctccatc   120
atccgtgacc ggggacccat gtatgatgac cccaccctgc ctgaaggctg acacggaag    180
cttaagcaaa ggaaatctgg ccgctctgct ggaagtatg atgtgtattt gatcaatccc    240
cagggaaaag cctttcgctc taaagtggag ttgattgcgt acttcgaaaa ggtaggcgac    300
acatccctgg accctaatga ttttgacttc acggtaactg ggagagggag ccctccccgg    360
cgagagcaga aaccacctgg atccagtggc agctctgggc caagaaaaa gcggaaggtg    420
ccggggagtg tggtggcagc cgctgccgcc gaggccaaaa agaaagccgt gaaggagtct    480
tctatccgat ctgtgcagga gaccgtactc cccatcaaga agcgcaagac ccgggagacg    540
gtc                                                                 543

SEQ ID NO: 4              moltype = DNA   length = 540
FEATURE                   Location/Qualifiers
misc_feature              1..540
                          note = miniMeCP2
source                    1..540
                          mol_type = other DNA
                          organism = synthetic construct
SEQUENCE: 4
gccgccgccg ccgccgccgc gccgagcgga ggaggaggag gaggcgagga ggagagactg    60
gaagaaaagc cggctgtgcc ggaagcttct gcctcccca acagcggcg ctccatcatc    120
cgtgaccggg gacccatgta tgatgacccc accctgcctg aaggctggac acggaagctt    180
aagcaaagga aatctggccg ctctgctggg aagtatgatg tgtatttgat caatcccag    240
ggaaaagcct ttcgctctaa agtggagttg attgcgtact tcgaaaaggt aggcgacaca    300
tccctggacc ctaatgattt tgacttcacg gtaactggga gagggagccc ctccggcga    360
gagcagaaac acctggatc cagtggcagc tctgggccca gaaaaaagcg gaaggtgccg    420
gggagtgtgg tggcagccgc tgccgccgag gccaaaaaga aagccgtgaa ggagtcttct    480
atccgatctg tgcaggagac cgtactcccc atcaagaagc gcaagacccg ggagacggtc    540

SEQ ID NO: 5              moltype = AA    length = 10
FEATURE                   Location/Qualifiers
REGION                    1..10
                          note = Myc Tag
source                    1..10
                          mol_type = protein
                          organism = synthetic construct
SEQUENCE: 5
EQKLISEEDL                                                           10

SEQ ID NO: 6              moltype = DNA   length = 30
FEATURE                   Location/Qualifiers
misc_feature              1..30
                          note = Myc Tag
source                    1..30
                          mol_type = other DNA
                          organism = synthetic construct
SEQUENCE: 6
gaacaaaaac tcatctcaga agaggatctg                                     30

SEQ ID NO: 7              moltype =   length =
SEQUENCE: 7
000

SEQ ID NO: 8              moltype =   length =
SEQUENCE: 8
000

SEQ ID NO: 9              moltype =   length =
SEQUENCE: 9
000

SEQ ID NO: 10             moltype =   length =
SEQUENCE: 10
000

SEQ ID NO: 11             moltype =   length =
SEQUENCE: 11
000

SEQ ID NO: 12             moltype =   length =
SEQUENCE: 12
000

SEQ ID NO: 13             moltype = DNA   length = 175
FEATURE                   Location/Qualifiers
```

```
misc_feature              1..175
                          note = Reg2 sequence
source                    1..175
                          mol_type = other DNA
                          organism = synthetic construct
SEQUENCE: 13
ctgttctagc ccccaaagag ttttctgtgc ttgcttttga aacttgaagt cttgaaaacc    60
aaagacatag atgtgaaaat tttaggcagt gtaagctgat agcacaagtt ctggcgactc   120
acaattatgc tgtgaatttt acaaaaagaa gcagtaatct acctcagccg ataac        175

SEQ ID NO: 14             moltype = DNA   length = 221
FEATURE                   Location/Qualifiers
misc_feature              1..221
                          note = RDH1pA
source                    1..221
                          mol_type = other DNA
                          organism = synthetic construct
SEQUENCE: 14
agctcgctga tcagcctcac aagaataaag gcagctgttg tctcttcaga agtagctttg    60
cactttccta aactaggaat atcaccagga ctgttactca atgtgtgctg caggaaagct   120
gatatattta aaaacaaaag gtgtaaccta tttattatat aaagagtttg ccttataaat   180
ttacataaaa atgtccgttt gtgtcttttg ttgtaaaaat c                       221

SEQ ID NO: 15             moltype = DNA   length = 89
FEATURE                   Location/Qualifiers
misc_feature              1..89
                          note = Other miRNA binding sites found in RDH1pA
source                    1..89
                          mol_type = other DNA
                          organism = synthetic construct
SEQUENCE: 15
acaagaataa aggcagctgt tgtctcttca gaagtagctt tgcactttc taaactagga    60
atatcaccag gactgttact caatgtgtg                                      89

SEQ ID NO: 16             moltype = DNA   length = 110
FEATURE                   Location/Qualifiers
misc_feature              1..110
                          note = MeCP2 downstream pA
source                    1..110
                          mol_type = other DNA
                          organism = synthetic construct
SEQUENCE: 16
gaaagcactg atatatttaa aaacaaaagg tgtaacctat ttattatata aagagtttgc    60
cttataaatt tacataaaaa tgtccgtttg tgtcttttgt tgtaaaaatc              110

SEQ ID NO: 17             moltype = DNA   length = 398
FEATURE                   Location/Qualifiers
misc_feature              1..398
                          note = Regulatory Sequence
source                    1..398
                          mol_type = other DNA
                          organism = synthetic construct
SEQUENCE: 17
agctcgctga tcagcctcac aagaataaag gcagctgttg tctcttcaga agtagctttg    60
cactttccta aactaggaat atcaccagga ctgttactca atgtgtggtc gacctgttct   120
agcccccaaa gagttttctg tgcttgcttt tgaaacttga agtcttgaaa accaaagaca   180
tagatgtgaa aattttaggc agtgtaagct gatagcacaa gttctggcga ctcacaatta   240
tgctgtgaat tttacaaaaa gaagcagtaa tctacctcag ccgataacga aagcactgat   300
atatttaaaa acaaaggtg taacctattt attatataaa gagtttgcct tataaattta   360
cataaaaatg tccgtttgtg tcttttgttg taaaaatc                           398

SEQ ID NO: 18             moltype = DNA   length = 104
FEATURE                   Location/Qualifiers
misc_feature              1..104
                          note = 5' AAV ITR
source                    1..104
                          mol_type = other DNA
                          organism = synthetic construct
SEQUENCE: 18
tgcgcgctcg ctcgctcact gaggccgccc gggcaaagcc cgggcgtcgg gcgacctttg    60
gtcgcccggc ctcagtgagc gagcgagcgc gcagagaggg agtg                    104

SEQ ID NO: 19             moltype = DNA   length = 106
FEATURE                   Location/Qualifiers
misc_feature              1..106
                          note = 5' AAV ITR
source                    1..106
                          mol_type = other DNA
                          organism = synthetic construct
```

```
SEQUENCE: 19
ctgcgcgctc gctcgctcac tgaggccgcc ggcccaaagg gccggcgtcg ggcgaccttt    60
ggtcgcccgg cctcagtgag cgagcgagcg cgcagagagg gagtgg                  106

SEQ ID NO: 20           moltype = DNA   length = 130
FEATURE                 Location/Qualifiers
misc_feature            1..130
                        note = 3' AAV ITR
source                  1..130
                        mol_type = other DNA
                        organism = synthetic construct
SEQUENCE: 20
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                         130

SEQ ID NO: 21           moltype = DNA   length = 145
FEATURE                 Location/Qualifiers
misc_feature            1..145
                        note = 3' AAV ITR
source                  1..145
                        mol_type = other DNA
                        organism = synthetic construct
SEQUENCE: 21
aggaacccct agtgatggag ttggccactc cctctctgcg cgctcgctcg ctcactgagg    60
ccgggcgacc aaaggtcgcc cgacgccggc cctttgggcc ggcggcctca gtgagcgagc   120
gagcgcgcag agagggagtg gccaa                                        145

SEQ ID NO: 22           moltype = DNA   length = 426
FEATURE                 Location/Qualifiers
misc_feature            1..426
                        note = meP426 Promoter
source                  1..426
                        mol_type = other DNA
                        organism = synthetic construct
SEQUENCE: 22
ataggcgcca agagcctaga cttccttaag cgccagagtc cacaagggcc cagttaatcc    60
tcaacattca aatgctgccc acaaaaccag cccctctgtg ccctagccgc ctcttttttc   120
caagtgacag tagaactcca ccaatccgca gctgaatggg gtccgcctct tttccctgcc   180
taaacagaca ggaactcctg ccaattgagg gcgtcaccgc taaggctccg ccccagcctg   240
ggctccacaa ccaatgaagg gtaatctcga caaagagcaa ggggtggggc gcgggcgcgc   300
aggtgcagca gcacacaggc tggtcgggag ggcggggcgc gacgtctgcc gtgcgggtc   360
ccggcatcgg ttgcgcgcgc gctccctcct ctcggagaga ggctgtggt aaaacccgtc   420
cggaaa                                                             426

SEQ ID NO: 23           moltype = DNA   length = 164
FEATURE                 Location/Qualifiers
misc_feature            1..164
                        note = JeT promoter
source                  1..164
                        mol_type = other DNA
                        organism = synthetic construct
SEQUENCE: 23
gggcggagtt agggcggagc caatcagcgt gcgccgttcc gaaagttgcc ttttatggct    60
gggcggagaa tgggcggtga acgccgatga ttatataagg acgcgccggg tgtggcacag   120
ctagttccgt cgcagccggg atttgggtcg cggttccttg ttgt                   164

SEQ ID NO: 24           moltype = DNA   length = 225
FEATURE                 Location/Qualifiers
misc_feature            1..225
                        note = meP229 Promoter
source                  1..225
                        mol_type = other DNA
                        organism = synthetic construct
SEQUENCE: 24
caattgaggg cgtcaccgct aaggctccgc cccagcctgg gctccacaac caatgaaggg    60
taatctcgac aaagagcaag gggtggggcg cgggcgcgca ggtgcagcag cacacaggct   120
ggtcgggagg gcggggcgcg acgtctgccg tgcgggtcc cggcatcggt tgcgcgcgcg   180
ctccctcctc tcggagagag gctgtggta aaacccgtcc ggaaa                   225

SEQ ID NO: 25           moltype = DNA   length = 796
FEATURE                 Location/Qualifiers
misc_feature            1..796
                        note = CBh promoter
source                  1..796
                        mol_type = other DNA
                        organism = synthetic construct
SEQUENCE: 25
tacataaactt acggtaaatg gcccgcctgg ctgaccgccc aacgaccccc gcccattgac    60
```

```
gtcaatagta acgccaatag ggactttcca ttgacgtcaa tgggtggagt atttacggta    120
aactgcccac ttggcagtac atcaagtgta tcatatgcca agtacgcccc ctattgacgt    180
caatgacggt aaatggcccg cctggcattt gcccagtac atgaccttat gggactttcc     240
tacttggcag tacatctacg tattagtcat cgctattacc atggtcgagg tgagcccac     300
gttctgcttc actctcccca tctccccccc ctccccacca ccaattttgt atttatttat    360
ttttaatta ttttgtgcag cgatgggggc ggggggggg ggggggcgcg cgccaggcgg      420
ggcggggcgg ggcgagggc ggggcgggc gaggcggaga ggtgcggcgg cagccaatca      480
gagcggcgc ctccgaaagt ttcctttat ggcgaggcgg cggcggcggc ggccctataa      540
aaagcgaagc gcgcggcggg cgggagtcgc tgcgacgctg ccttcgcccc gtgccccgct    600
ccgccgccgc ctcgcgccgc ccgccccggc tctgactgac cgcgttactc ccacaggtga    660
gcgggcggga cggcccttct cctccgggct gtaattagct gagcaagagg taagggttta    720
agggatggtt ggttggtggg gtattaatgt ttaattacct ggagcacctg cctgaaatca    780
cttttttttca ggttgg                                                   796

SEQ ID NO: 26          moltype = DNA   length = 123
FEATURE                Location/Qualifiers
misc_feature           1..123
                       note = SV40 PolyA sequence
source                 1..123
                       mol_type = other DNA
                       organism = synthetic construct
SEQUENCE: 26
tgtttattgc agcttataat ggttacaaat aaagcaatag catcacaaat ttcacaaata     60
aagcattttt ttcactgcat tctagttgtg tttgtccaa actcatcaat gtatcttatc    120
atg                                                                  123

SEQ ID NO: 27          moltype = DNA   length = 1682
FEATURE                Location/Qualifiers
misc_feature           1..1682
                       note = self-comp MeP426-miniMECP2-myc-reg2-RDH1PA
source                 1..1682
                       mol_type = other DNA
                       organism = synthetic construct
SEQUENCE: 27
tgcgcgctcg ctcgctcact gaggccgccc gggcaaagcc cgggcgtcgg gcgacctttg     60
gtcgcccggc ctcagtgagc gagcgagcgc gcagagaggg agtggggttc ggtacccata    120
ggcgccaaga gcctagactt ccttaagcgc cagagtccac aagggcccag ttaatcctca    180
acattcaaat gctgcccaca aaaccagccc ctctgtgccc tagccgcctc ttttttccaa    240
gtgacagtag aactccacca atccgcagct gaatgcctc ccctcttt cctgcctaa       300
acagacagga actcctgcca attgagggcg tcaccgctaa ggctccgccc cagcctgggc    360
tccacaacca atgaagggta atctcgacaa agagcaaggg gtggggcgcg ggcgcgcagg    420
tgcagcagca cacaggctgg tcgggagggc ggggcgcgac gtctgccgtg cggggtcccg    480
gcatcggttg cgcgcgcgct ccctcctctc ggagagaggg ctgtggtaaa accgtcccgg    540
aaaccatggc cgccgccgcc gccgccgcgc cgagcggagg aggaggagga ggcgaggagg    600
agagactgga agaaaagccg gctgtgccgg aagcttctgc ctcccccaaa cagcggcgct    660
ccatcatccg tgaccgggga cccatgtatg atgaccccca cctgcctgaa ggctggacac    720
ggaagcttaa gcaaaggaaa tctgccgct ctgctggaaa gtatgatgtg tattgatca     780
atccccaggg aaaagccttt cgctctaaag tggagttgat tgcgtacttc gaaaaggtag    840
gcgacacatc cctggaccct aatgattttg acttcacggt aactgggaga gggagccct    900
cccggcgaga gcagaaacca cctggatcca gtggcagctc tgggcccaag aaaaagcgga    960
aggtgcggg gagtgtggtg gcagccgctg ccgccgaggc caaaaagaaa gccgtgaagg   1020
agtcttctat ccgatctgtg caggagaccg tactcccccat caagaagcgc aagacccggg   1080
agacggtcgg gagctccggc agttctggag aacaaaaaact catctcagaa gaggatctgg   1140
tcgactagag ctcgctgatc agcctcacaa gaataaggc agctgttgtc tcttcagaag    1200
tagctttgca cttttctaaa ctaggaatat caccaggact gttactcaat gtgtggtcga   1260
cctgttctag cccccaaaga gttttctgtg cttgcttttg aaacttgaag tcttgaaaac   1320
caaagacata gatgtgaaaa ttttaggcag tgtaagctga tagcacaagt tctggcgact   1380
cacaattatg ctgtgaattt tacaaaaaga agcagtaatc tacctcagcc gataacgaaa   1440
gcactgatat atttaaaaac aaaaggtgta acctatttat tatataaaga gtttgcctta   1500
taaatttaca taaaaatgtc cgtttgtgtc ttttgttgta aaaatcacgc gtaggaaccc   1560
ctagtgatgg agttggccac tccctctctg cgcgctcgct cgctcactga ggccgggcga   1620
ccaaaggtcg cccgacgccc gggctttgcc cgggcggcct cagtgagcga gcgagcgcgc   1680
ag                                                                  1682

SEQ ID NO: 28          moltype = DNA   length = 545
FEATURE                Location/Qualifiers
misc_feature           1..545
                       note = miniMECP2
source                 1..545
                       mol_type = other DNA
                       organism = synthetic construct
SEQUENCE: 28
ccatggccgc cgccgccgcc gccgcgccga gcggaggagg aggaggaggc gaggaggaga     60
gactggaaga aaagccggct gtgccggaag cttctgcctc ccccaaacag cggcgctca    120
tcatccgtga ccggggaccc atgtatgatg accccaccct gcctgaaggc tggacacga    180
agcttaagca aaggaaatct ggccgctctg ctgggaagta tgatgtgtat ttgatcaatc    240
cccagggaaa agcctttcgc tctaaagtgg agttgattgc gtacttcgaa aaggtaggcg    300
acacatccct ggaccctaat gattttgact tcacggtaac tgggagaggg agcccctccc    360
ggcgagagca gaaaccacct ggatccagtg gcagctctgg gcccaagaaa aagcggaagg    420
```

```
tgccggggag tgtggtggca gccgctgccg ccgaggccaa aaagaaagcc gtgaaggagt    480
cttctatccg atctgtgcag gagaccgtac tccccatcaa gaagcgcaag acccgggaga    540
cggtc                                                               545

SEQ ID NO: 29           moltype = DNA  length = 1660
FEATURE                 Location/Qualifiers
misc_feature            1..1660
                        note = rAAV Sequence
source                  1..1660
                        mol_type = other DNA
                        organism = synthetic construct
SEQUENCE: 29
ctgcgcgctc gctcgctcac tgaggccgcc ggcccaaagg gccggcgtcg ggcgaccttt     60
ggtcgcccgg cctcagtgag cgagcgagcg cgcagagagg gagtggagat ctgaattcgg    120
tacccatagg cgccaagagc ctagacttcc ttaagcgcca gagtccacaa gggcccagtt    180
aatcctcaac attcaaatgc tgcccacaaa accagcccct ctgtgcccta gccgcctctt    240
ttttccaagt gacagtagaa ctccaccaat ccgcagctga atggggtccg cctcttttcc    300
ctgcctaaac agacaggaac tcctgccaat tgagggcgtc accgctaagg ctccgcccca    360
gcctgggctc cacaaccaat gaagggtaat ctcgacaaag agcaaggggt ggggcgcggg    420
cgcgcaggtg cagcagcaca caggctggtc ggggaggcgg ggcgcgacgt ctgccgtgcg    480
gggtcccggc atcggttgcg cgcgcgctcc ctcctctcgg agagagggct gtggtaaaac    540
ccgtccggaa accatggccg ccgccgccgc cgccgcgccg agcggaggag gaggaggagg    600
cgaggaggag agactggaag aaaagccggc tgtgccggaa gcttctgcct ccccaaaca     660
gcggcgctcc atcatccgtg accggggacc catgtatgat gacccacccc tgcctgaagg    720
ctggacacgg aagcttaagc aaaggaaatc tggccgctct gctgggaagt atgatgtgta    780
tttgatcaat ccccagggaa aagcctttcg ctctaaagtg gagttgattg cgtacttcga    840
aaaggtaggc gacacatccc tggaccctaa tgattttgac ttcacggtaa ctggagagg    900
gagcccctcc cggcgagagc agaaaccacc tggatccagt ggcagctctg ggcccaagaa    960
aaagcggaag gtgccgggga gtgtggtggc agccgctgcc gccgaggcca aaagaaagc   1020
cgtgaaggag tcttctatcc gatctgtgca ggagaccgta ctccccatca agaagcgcaa   1080
gacccgggag acggtctaga gctcgctgat cagcctcaca agaataaagg cagctgttgt   1140
ctcttcagaa gtagctttgc acttttctaa actaggaata tcaccaggac tgttactcaa   1200
tgtgtggtcg acctgttcta gcccccaaag agttttctgt gcttgctttt gaaacttgaa   1260
gtcttgaaaa ccaaagacat agatgtgaaa attttaggca gtgtaagctg atagcacaag   1320
ttctggcgac tcacaattat gctgtgaatt ttacaaaaag aagcagtaat ctacctcagc   1380
cgataacgaa agcactgata tatttaaaaa caaaaggtgt aacctattta ttatataaag   1440
agtttgcctt ataaatttac ataaaaatgt ccgtttgtgt cttttgttgt aaaaatcacg   1500
cgtgcatgca gatctaggaa cccctagtga tggagttggc cactccctct ctgcgcgctc   1560
gctcgctcac tgaggccggg cgaccaaagg tcgcccgacg ccggcccttt gggccggcgg   1620
cctcagtgag cgagcgagcg cgcagagagg gagtggccaa                         1660

SEQ ID NO: 30           moltype = DNA  length = 145
FEATURE                 Location/Qualifiers
misc_feature            1..145
                        note = 5' ITR Sequence
source                  1..145
                        mol_type = other DNA
                        organism = synthetic construct
SEQUENCE: 30
aggaacccct agtgatggag ttggccactc cctctctgcg cgctcgctcg ctcactgagg     60
ccgccggccc aaagggccgg cgtcgggcga cctttggtcg cccggcctca gtgagcgagc    120
gagcgcgcag agggagtg gccaa                                            145
```